US011413372B2

(12) United States Patent
Daniel et al.

(10) Patent No.: US 11,413,372 B2
(45) Date of Patent: Aug. 16, 2022

(54) COMPOSITIONS DERIVED FROM PLACENTA AND METHODS OF PRODUCING THE SAME

(71) Applicant: StimLabs LLC, Roswell, GA (US)

(72) Inventors: John Daniel, Milton, GA (US); Sarah Griffiths, Atlanta, GA (US); Richard Berg, Arroyo Grande, CA (US)

(73) Assignee: StimLabs LLC, Roswell, GA (US)

( * ) Notice: Subject to any disclaimer, the term of this patent is extended or adjusted under 35 U.S.C. 154(b) by 145 days.

(21) Appl. No.: 15/760,757

(22) PCT Filed: Sep. 16, 2016

(86) PCT No.: PCT/US2016/052319
§ 371 (c)(1),
(2) Date: Mar. 16, 2018

(87) PCT Pub. No.: WO2017/049215
PCT Pub. Date: Mar. 23, 2017

(65) Prior Publication Data
US 2018/0280572 A1    Oct. 4, 2018

Related U.S. Application Data

(60) Provisional application No. 62/334,440, filed on May 10, 2016, provisional application No. 62/220,227, filed on Sep. 17, 2015.

(51) Int. Cl.
| | | |
|---|---|---|
| *A61L 27/36* | (2006.01) | |
| *A61K 35/50* | (2015.01) | |
| *A61L 27/56* | (2006.01) | |
| *A61L 15/40* | (2006.01) | |
| *C12N 5/073* | (2010.01) | |

(52) U.S. Cl.
CPC .......... *A61L 27/3604* (2013.01); *A61K 35/50* (2013.01); *A61L 15/40* (2013.01); *A61L 27/3691* (2013.01); *A61L 27/56* (2013.01); *C12N 5/0605* (2013.01); *C12N 2533/92* (2013.01)

(58) Field of Classification Search
CPC ... A61L 27/3604; A61L 15/40; A61L 27/3691
See application file for complete search history.

(56) References Cited

U.S. PATENT DOCUMENTS

| | | | |
|---|---|---|---|
| 8,231,908 B2 | 7/2012 | Kinoshita et al. | |
| 8,323,701 B2 | 12/2012 | Daniel et al. | |
| 8,409,626 B2 | 4/2013 | Daniel et al. | |
| 8,414,929 B2 | 4/2013 | Nikaido et al. | |
| 8,685,732 B2 | 4/2014 | Perez et al. | |
| 8,709,494 B2 | 4/2014 | Daniel | |
| 8,932,641 B2 | 1/2015 | Nikaido et al. | |
| 9,084,767 B2 | 7/2015 | Daniel et al. | |
| 9,186,382 B2 * | 11/2015 | Daniel ................ | A61L 27/3683 |
| 9,486,316 B2 | 11/2016 | Horton et al. | |
| 9,539,104 B2 | 1/2017 | Horton et al. | |
| 11,116,871 B2 | 9/2021 | Daniel et al. | |
| 2005/0107876 A1 | 5/2005 | Kim et al. | |
| 2011/0189301 A1 | 8/2011 | Yang et al. | |
| 2012/0083900 A1 | 4/2012 | Samaniego et al. | |
| 2013/0136773 A1* | 5/2013 | Horton ................ | A61L 27/3604 424/400 |
| 2013/0218274 A1 | 8/2013 | Spencer et al. | |
| 2014/0050788 A1 | 2/2014 | Daniel et al. | |
| 2014/0186461 A1 | 7/2014 | Broussard | |
| 2015/0216910 A1 | 8/2015 | Horton et al. | |
| 2016/0136328 A1 | 5/2016 | LeVaughn et al. | |
| 2017/0086961 A1 | 3/2017 | Ganey | |
| 2017/0246348 A1 | 8/2017 | Daniel et al. | |

FOREIGN PATENT DOCUMENTS

| | | |
|---|---|---|
| EP | 3349812 B1 | 1/2021 |
| WO | 3310722 A2 | 6/1993 |
| WO | 2004028584 A1 | 4/2004 |
| WO | 2006026325 A2 | 3/2006 |
| WO | 2007114809 A1 | 10/2007 |
| WO | 2009033160 A1 | 3/2009 |
| WO | 2012088396 A2 | 6/2012 |

(Continued)

OTHER PUBLICATIONS

Zelen et al. A prospective, randomised, controlled, multi-centre comparative effectiveness study of healing using dehydrated human amnion/chorion membrane allograft . . . . Int Wound Journal, 12(6), 2014, p. 724-732. (Year: 2014).*

Arpino, A., et al., "The role of TIMPs in regulation of extracellular matrix proteolysis," Matrix Biol, 2015, 44-66:247-54.

Bryant-Greenwood, G., "The Extracellular Matrix of the Human Fetal Membranes: Structure and Function," Placenta, 1998, 19(1):1-11.

Goa, K.L. & Benfield, P., "Hyaluronic Acid: A Review of its Pharmacology and Use as a Surgical Aid in Ophthalmology, and its Therapeutic Potential in Joint Disease and Wound Healing," Drugs, 1994, 47(3):536-66.

(Continued)

*Primary Examiner* — Kara D Johnson

(74) *Attorney, Agent, or Firm* — McNeill Baur PLLC

(57) ABSTRACT

Compositions comprising unseparated amnion/chorion derived from the placenta and methods of preparing and using those compositions are provided. Washing or preservation of placental tissue according to the methods of the disclosure may allow for one or more benefits such as more efficient removal of blood remnants, retention of wound healing and tissue regeneration components, better handling characteristics, increased absorption potential, or improved healing capacity. The present invention also includes methods of healing a wound of the skin, eye, nerve, tendon, or dura comprising applying the compositions of the invention to the wound.

19 Claims, No Drawings

(56) References Cited

FOREIGN PATENT DOCUMENTS

| | | |
|---|---|---|
| WO | 2012112410 A2 | 8/2012 |
| WO | 2013049052 A2 | 4/2013 |
| WO | 2013082412 A1 | 6/2013 |
| WO | 2016081386 A1 | 5/2016 |
| WO | 2017049210 A1 | 3/2017 |
| WO | 2017049215 A1 | 3/2017 |
| WO | 2017112934 A1 | 6/2017 |

OTHER PUBLICATIONS

Hieber, A., et al., "Detection of Elastin in the Human Fetal Membranes: Proposed Molecular Basis for Elasticity," Placenta, 1997,18(4):301-12.
Jacobson, A., et al., "Expression of human hyaluronan synthases in response to external stimuli," Biochem J, 2000, 348(Pt 1):29-35.
Keene, D., "Type VII Collagen Forms an Extended Network of Anchoring Fibrils," J Cell Biol, 1987, 104(3):611-21.
Laurent, T., et al., "Hyaluronan in inflammatory joint disease," Acta Orthop Scand, 1995, 66:116-120.
Malak, T.M., et al., "Confocal Immunofluorescence Localization of Collagen Types I, III, IV, V and VI and their Ultrastructural Organization in Term Human Fetal Membranes," Placenta, 1993, 14(4):385-406.
Mamede, A.C., et al., "Amniotic membrane: from structure and functions to clinical applications," Cell Tissue Res, 2012, 349(2):447-58.
Meinert, M., et al., "Proteoglycans and hyaluronan in human fetal membranes," Am J Obstet Gynecol, 2001, 184 (4):679-85.
Necas, J., et al., "Hyaluronic acid (hyaluronan): a review," Veterinarni Medicina, 2008 53(8):397-411.
Parolini, O., et al., Chapter I, "Human Term Placenta as a Therapeutic Agent: From the First Clinical Applications to Future Perspectives," In Human Placenta: Structure and Development, Circulation and Functions. E. Berven & A. Freberg (Eds.), Nova Science Publishers, Inc., 2010, pp. 1-49.
Rousselle, P., et al., "Laminin 5 Binds the NC-1 Domain of Type VII Collagen," J Cell Biol, 1997, 138(3):719-28.
Smith, J. & Ockleford, C.D., "Laser Scanning Confocal Examination and Comparison of Nidogen (Entactin) with Laminin in Term Human Amniochorion," Placenta, 1994, 15(1):95-106.
Tseng, S., et al., "How Does Amniotic Membrane Work?" The Ocular Surface, 2004, 2(3):177-87.
Vishwakarma, G., et al., "Amniotic Arthroplasty for Tuberculosis of the Hip," J Bone Joint Surg Br, 1986, 68(1):68-74.
Visse, R. & Nagase, H., "Matrix Metalloproteinases and Tissue Inhibitors of Metalloproteinases: Structure, Function, and Biochemistry," Circ Res, 2003, 92(8):827-39 and Supplementary Data pp. 1-9.
Werner, S. & Grose, R., "Regulation of Wound Healing by Growth Factors and Cytokines," Physiol Rev., 2003, 83 (3):835-70.
Abshier, S., "A closer look at the potential of placental membrane grafts for chronic diabetic foot ulceration," Podiatry Today, 2015, 28(11):20-26, 12 printed pages.
MiMedx Purion Process, accessed from https://mimedx.com/purion-process/ on Sep. 9, 2019, 3 printed pages.
Nichols, F. and Overly A., "Novel Approach for Enterocutaneous Fistula Treatment with the Use of Viable Cryopreserved Placental Membrane," Case Rep Surg. 2016, Article ID 8797691, 4 pages.
Robson, M., et al., "Quantitative Comparison of Biological Dressings," J Surg Res. 1973, 14(5):431-4.
Baergen, R., Chapter 6, "Histology of the Chorionic Villi, Fetal Membranes, and Umbilical Cord," Manual of Benirschke and Kaufmann's Pathology of the Human Placenta, Springer Science+Business Media, Inc., 2005, pp. 80-95.
Baergen, R., et al., Chapter 7, "Overview and Microscopic Survey of the Placenta," Manual of Pathology of the Human Placenta, Springer + Business Media, LLC, 2011, pp. 85-108.
Benirschke K., et al., Chapter 11, "Anatomy and Pathology of the Placental Membranes," Pathology of the Human Placenta, Springer-Verlag Berlin Heidelberg, 2012, pp. 249-307.
Bhushan, K., et al., "Amniotic membrane & its structure, features and uses in dentistry—a brief review," Int J Adv Res, 2015, 3(11):354-60.
Bourne, G., "The Foetal Membranes, A Review of the Anatomy of Normal Amnion and Chorion and Some Aspects of Their Function," Postgrad. Med. J., 1962, 38:193-201.
Bujang-Safawi, E., et al., "Dried irradiated human amniotic membrane as a biological dressing for facial burns—A 7-year case series," Burns, 2010, 36(6):876-82.
Davis, J.S., "Skin Transplantation. With a Review of 550 Cases at the Johns Hopkins Hospital," The Johns Hopkins Hospital Reports, vol. XV, pp. 308-396, 91 pages, 1910.
De Rötth, A., "Plastic Repair of Conjunctival Defects with Fetal Membranes," Arch Ophthalmol, 1940, 23(3):522-525.
Dino, B., et al., "Human Amnion: The Establishment of an Amnion Bank and its Practical Applications in Surgery," J Philipp Med Assoc, 1966, 42(7):357-66.
Douglas, B., "Homografts of Fetal Membranes as a Covering for Large Wounds—Especially Those From Burns," J Tn State Med Assoc, 1952, 45(6):230-5.
Dua, H., et al., "Amniotic membrane transplantation," Br J Ophthalmol, 1999, 83:748-752.
Fetterolf D., et al., "Scientific and Clinical Support for the Use of Dehydrated Amniotic Membrane in Wound Management," Wounds, 2012, 24(10):299-307.
Ganatra, M.A., "Amniotic Membrane in Surgery," J Pak Med Assoc, 2003, 53(1), 7 pages.
Ganatra, M.A., "Method of Obtaining and Preparation of Fresh Human Amniotic Membrane for Clinical Use," J Pak Med Assoc, 1996, 46(6):126-8, 5 pages.
Gibbons G.W., "Grafix®, a Cryopreserved Placental Membrane, for the Treatment of Chronic/Stalled Wounds," Adv Wound Care, 2015, 4(9):534-44.
Hopkinson, A., et al., "Proteomic Analysis of Amniotic Membrane Prepared for Human Transplantation: Characterization of Proteins and Clinical Implications," J Proteome Res, 2006, 5(9):2226-35.
Hsu, G.., "Utilizing Dehydrated Human Amnion/Chorion Membrane Allograft in Transcanal Typanoplasty," Otolaryngology, 2014, 4: 161. doi:10.4172/2161-119X.1000161, 3 pages.
Hu, D., et al., "Staining Characteristics of Preserved Human Amniotic Membrane," Cornea, 2003, 22(1):37-40.
International Preliminary Report on Patentability for International Application No. PCT/US2016/052314, dated Mar. 20, 2018, 10 pages.
International Preliminary Report on Patentability for International Application No. PCT/US2016/052319, dated Mar. 20, 2018, 10 pages.
International Search Report and Written Opinion of International Application No. PCT/US2016/052314, dated Nov. 30, 2016, 19 pages.
International Search Report and Written Opinion of International Application No. PCT/US2016/052319, dated Feb. 12, 2016, 20 pages.
John, T., "Human amniotic membrane transplantation: Past, present, and future," Ophthalmol Clin N Am, 2003, 16 (1):43-65.
Kandavel, G., et al., "Staining Properties of Deepithelialized Human Amniotic Membrane," Cornea, 2005, 24(7):853-56.
Klen, R., "Preparation of Chorion and/or amnion grafts used in burns," Transactions of the Third International Congress on Research in Burns, 1970, pp. 289-292.
Koh, J., et al., "The Expression of TIMPs in Cryo-Preserved and Freeze-Dried Amniotic Membrane," Curr Eye Res, 2007, 32(7-8):611-6.
Koob, T., et al., "Angiogenic properties of dehydrated human amnion/chorion allografts: therapeutic potential for soft tissue repair and regeneration," Vasc Cell 2014, 6:10, doi: 10.1186/2045-824X-6-10, 10 pages.
Koob, T., et al., "Biological properties of dehydrated human amnion/chorion composite graft: implications for chronic wound healing," Int Wound J, 2013, 10(5):493-500.

(56) References Cited

OTHER PUBLICATIONS

Koob, T., et al., "Cytokines in single layer amnion allografts compared to multilayer amnion/chorion allografts for wound healing," J Biomed Mater Res B Appl Biomater, 2015, 103B:1133-1140.
Koob, T., et al., "Properties of dehydrated human amnion/chorion composite grafts: Implications for wound repair and soft tissue regeneration," J Biomed Mater Res, Part B, 2014:102(6):1353-1362, doi:10.1002/jbm.b.33141, 10 pages.
Kruse, F., et al., "Cryopreserved human amniotic membrane for ocular surface reconstruction," Graefe's Arch Clin Exp Ophthalmol, 2000, 238(1):68-75.
Libera. R., et al. "Assessment of the use of cryopreserved x freeze-dried amniotic membrane (AM) for reconstruction of ocular surface in rabbit model." Arq Bras Oftalmol, 2008, 71(5):669-73.
Mohammadi, A., et al., Chapter 18, "How Does Human Amniotic Membrane Help Major Burn Patients Who Need Skin Grafting: New Experiences," Skin Grafts—Indications, Applications and Current Research, Ed. M. Spear, In Tech, 2011, pp. 265-276, 13 pages.
Nakamura, T., et al., "Novel clinical application of sterilized, freeze-dried amniotic, membrane to treat patients with pterygium," Acta Ophthalmol Scand, 2006, 84(3):401-5.
Nakamura, T., et al., "Sterilized, Freeze-Dried Amniotic Membrane: A Useful Substrate for Ocular Surface Reconstruction," IOVS, 2004, 45(1):93-99.
Niknejad, H., et al., "Properties of the Amniotic Membrane for Potential Use in Tissue Engineering," Eur Cell Mater, 2008, 15:88-99.
Park, C., et al., "Immunosuppressive Property of Dried Human Amniotic Membrane," Ophthalmic Res, 2009, 41 (2):112-3, Epub 2008.
Reddy, U. et al., "In vitro sealing of punctured fetal membranes: Potential treatment for midtrimester premature rupture of membranes," Am J Obstet Gynecol, 2001, 185(5):1090-93.
Robson, M., et al., "Amniotic Membranes as a Temporary Wound Dressing," Surg Gynecol Obstet, 1973, 136(6): 904-6.
Rodriguez-Ares, M., et al., "Effects of lyophilization on human amniotic membrane," Acta Ophthalmol, 2009, 87 (4):396-403.
Sabella, N., "Use of the Fetal Membranes in Skin Grafting," Medical Record, A Weekly Journal of Medicine and Surgery, 1913, 83:478-80.
Stern, M., "The Grafting of Preserved Amniotic Membrane to Burned and Ulcerated Surfaces, Substituting Skin Grafts," JAMA, 1913, 60(13):973-4.
Tan, E., et al., "Structural and Biological Comparison of Cryopreserved and Fresh Amniotic Membrane Tissues," J Biomater Tissue Eng, 2014, 4(5):379-388.
Vishwakarma. G., et al., "Amniotic Arthroplasty for Tuberculosis of the Hip," J Bone Joint Surg Br, 68(1):68-74.
Zelen, C., et al., "A prospective, randomised, controlled, multicentre comparative effectiveness study of healing using dehydrated human amnion/chorion membrane allograft, bioengineered skin substitute or standard of care for treatment of chronic lower extremity diabetic ulcers," Int Wound J, 2015, 12(6):724-32.
Full Thickness Native Placental Membrane, StimLabs, MKTG18-019 Rev 01 (2019) (1 page).
Response to Examination Report in European Application No. 16771073.0, filed on Sep. 16, 2019 (11 pages).
Response to Examination Report in European Application No. 16775926.5, filed on Jan. 21, 2020 (15 pages).
Revita®, The First Intact Amniotic Membrane Allograft, StimLabs, accessed from https://www.stimlabs.com/revita, on Aug. 7, 2020 (7 pages).
Revita® Pamphlet, StimLabs, MKTG 19-007 Rev 01 (2019) (3 pages).
Revita® Wound Application Guide, Dehydrated Human Placental Membrane Allograft, StimLabs, MKTG 18-002 Rev 01 (2018) (2 pages).
Revita®, The Optimal Barrier Membrane, StimLabs, MKTG18-027 Rev 02 (2018) (2 pages).
Roy et al., "Intermediate layer contribution in placental membrane allografts", J. Tissue Eng Regen Med., pp. 1-10 (2020), plus supplemental figure 1.
"Clarification on Revita," StimLabs (2018), accessed from https://static1.squarespace.com/static/5798cb8c1b631b57d81149b3/t/5d6eb56ae3fdc7000173570f/1567536491665/Clarification+on+Revita.pdf on Jan. 26, 2021, 8 pages.
"NuShield™ Extraordinary Properties, Everyday Utility," NuShield-202 Brochure (2015), 2 pages.
"StimLabs Announces Enrollment of First Patient in Evaluating Efficacy of Full Thickness Placental Allograft, Revita®, in Lumbar Microdiscectomy Outcomes," PRNewswire.com (Jun. 19, 2018), accessed from https://www.prnewswire.com/news-releases/stimlabs-announces-enrollment-of-first-patient-in-evaluating-efficacy-of-full-thickness-placental-allograft-revita-in-lumbar-microdiscectomy-outcomes-300668450.html?tc=eml_cleartime on Jan. 26, 2021, 3 pages.
"Efficacy of a Full-Thickness Placental Allograft in Lumbar Microdiscectomy", ClinicalTrials.gov Identifier: NCT03536013 (May 24, 2018), accessed from https://www.clinicaltrials.gov/ct2/show/NCT03536013 on Jan. 26, 2021, 6 pages.
"Efficacy of Human Placental Graft in Diabetic Foot Ulcers", ClinicalTrials.gov Identifier: NCT03708029 (Oct. 16, 2018), accessed from https://www.clinicaltrials.gov/ct2/show/NCT03708029 on Jan. 26, 2021, 6 pages.
"LifeNet Health is reimagining wound healing with Matrion™, the first fully intact and complete placental membrane," PRNewswire.com (Nov. 4, 2020), accessed from https://www.prnewswire.com/news-releases/lifenet-health-is-reimagining-wound-healing-with-matrion-the-first-fully-intact-and-complete-placental-membrane-301166304.html on Feb. 19, 2021, 3 pages.
Response to Examination Report in European Application No. 16775926.5, filed on Oct. 29, 2020 (134 pages).
Response to Examination Report in Australian Application No. 2016324167, filed on Jan. 14, 2021 (14 pages).
Response to Examination Report in Australian Application No. 2016324167, filed on Mar. 12, 2021 (9 pages).
Revita™ Intact Human Placental Membrane, LBL16-012 Rev 01 (2016) (1 page).
Revita™ The First Full Thickness Placental Membrane Allograft, LBL16-014 Rev 01 (2016) (2 pages).
StimLabs Enters Regenerative Medicine Market with Two Groundbreaking Amniotic Tissue Products, Jul. 25, 2017 (accessed from https://www.prnewswire.com/news-releases/stimlabs-enters-regenerative-medicine-market-with-two-groundbreaking-amniotic-tissue-products-300493787.html on Aug. 4, 2021) (3 pages).
RayBio® Human Hemoglobin ELISA Kit, RayBiotech, Catalog #: ELH-Hgb, User Manual, Last revised Dec. 7, 2015 (12 pages).
RayBio® Human Hemoglobin ELISA Kit, RayBiotech, Catalog #: ELH-Hgb, User Manual, Last revised Jan. 29, 2021 (12 pages).
RayBio® Human Hemoglobin ELISA Kit, RayBiotech, Catalog #: ELH-Hgb, User Manual, Last revised Jul. 6, 2017 (12 pages).
RayBio® Human Hemoglobin ELISA Kit, RayBiotech, Catalog #: ELH-Hgb, User Manual, Last revised Jun. 14, 2021 (12 pages).
Ambiodisk®, Clearify™ Processed Office Based Amniotic Membrane Grafts, KB-SS-072219 Rev0 (2019) (https://www.katena.com/pub/media/contentmanager/content/literature-pdf/AmbioDisk_Information.pdf) (2 pages).
Katena, AMBIO2® AMBIO5® Clearify™ processed surgical amniotic membrane allografts, KB-SS-071919 Rev1 (2019) (https://199752-598097-raikfcquaxqncofqfm.stackpathdns.com/pub/media/contentmanager/content/literature-pdf/Clearify_Ambio2_Ambio5_Katena.pdf?=bi) (2 pages).
Katena, AMBI02® and AMBIO5® Allograft Instructions for Use, LBL19-009 Rev 05 (2021) (2 pages).
Katena, Clearify™ Processed Surgical Amniotic Membrane Grafts, AMBIO2® AMBIO5®, KB-SS-071919-Rev0 (2019) (2 pages).
Revita® Burn & Revita® Burn Clear Allograft Instructions for Use, StimLabs, LBL18-013 Rev 02 (2019) (2 pages).
Revita® Burn & Revita® Burn Clear Allograft Instructions for Use, StimLabs, LBL18-014 Rev 02 (2019) (2 pages).
Revita® Burn Clear Allograft Instructions for Use, StimLabs, LBL18-017 Rev 02 (2019) (2 pages).

(56) References Cited

OTHER PUBLICATIONS

Revita® Burn Clear Intact Human Placental Membrane, StimLabs, MKTG 19-013 Rev 03 (2021) (1 page).
Revita® Burn Clear Intact Human Placental Membrane, StimLabs, MKTG 19-015 Rev 01 (2019) (1 page).
Revita® Clear A Next Generation Human Placental Allograft, StimLabs, MKTG 19-001 Rev 02 (2021) (1 page).
Revita® Clear Allograft Instructions for Use Dehydrated Human Placental Tissue Allograft, StimLabs, LBL17-033 Rev 02 (2019) (2 pages).
Revita® Clear Allograft Instructions for Use Dehydrated Human Placental Tissue Allograft, StimLabs, LBL17-034 Rev 02 (2019) (2 pages).
Revita® Clear Full-Thickness Barrier Membrane, StimLabs, MKTG 20-002 Rev 02 (2020) (2 pages).
Revita® Clear Intact Human Placental Membrane, StimLabs, MKTG 19-016 Rev 02 (2021) (1 page).

\* cited by examiner

COMPOSITIONS DERIVED FROM PLACENTA AND METHODS OF PRODUCING THE SAME

CROSS REFERENCE TO RELATED APPLICATIONS

This application is a national phase entry pursuant to 35 U.S.C. § 371 of International Application No. PCT/US2016/52319 filed Sep. 16, 2016, which claims the benefit of priority of U.S. Provisional Application No. 62/220,227, filed Sep. 17, 2015, and U.S. Provisional Application No. 62/334,440, filed May 10, 2016, each of which is incorporated by reference herein in their entirety for any purpose.

FIELD

This application relates to compositions derived from placental tissue and methods of preparing and using those compositions.

INTRODUCTION AND SUMMARY

This application provides for compositions comprising unseparated amnion/chorion and methods of preparing and using those compositions.

Since the early 1900s, grafts derived from the placental membranes have been used in skin transplantation as wound dressings, patch grafts, and in the management of burns and ulcers. Placental grafts have also been used in a variety of other procedures, including tympanoplasty, arthroplasty, in the reconstruction of the oral cavity, bladder, vagina, and in the regeneration of the ocular surface and peripheral nerves.

The placenta includes the amniotic sac, which develops from extra-embryonic tissue and separates the developing fetus from the maternal endometrium. The amniotic sac includes a thin but resilient pair of membranes—the amnion and the chorion—separated by an intermediate (or spongy) layer. The amnion is the innermost membrane of the amniotic sac and is in contact with the amniotic fluid, the fetus, and the umbilical cord. The amnion is composed of four layers: an epithelial monolayer, a basement membrane, a compact layer, and a fibroblast layer. The chorion, which is loosely connected to the intermediate layer, forms the outermost layer of the amniotic sac separating the amnion from the maternal endometrium. The chorion is composed of three layers: a reticular layer, a basement membrane, and a trophoblast layer. The chorion is generally several times thicker than the amnion, but the amnion is understood to be stronger and stiffer than the chorion.

It is understood that during the second trimester of pregnancy as the placenta grows, the trophoblast layer of the chorion comes into contact with the capsular decidua layer (the portion of the maternal endometrium facing the uterine cavity). It is also understood that as the capsular decidua degenerates, the cells of the trophoblast layer of the chorion become intermingled with and morphologically indistinguishable from the remaining cells of the capsular decidua. In addition, maternal blood vessels are understood to often be present in the capsular decidua layer. K Benirschke et al., *Pathology of the Human Placenta*, DOI 10.1007/978-3-642-23941-0_11, © Springer-Verlag Berlin Heidelberg 2012; K. N. Baergen, *Manual of Pathology of the Human Placenta*, DOI 10.1007/978-1-4419-7494-5_7, © Springer Science+Business Media, LLC2011.

Placental membranes are complicated tissues composed of numerous components, such as growth factors, cells, and extracellular matrix molecules. Placental membranes are understood to possess many biological properties important for tissue regeneration and wound healing, such as promotion of cell migration and growth; low immunogenicity; and anti-fibrosis, anti-scarring, anti-microbial, anti-inflammatory, and anti-pain activities. Placental membranes may also serve as a scaffold for cell proliferation and differentiation.

Current methods of preparing placental membrane grafts involve manually separating the amnion from the chorion to allow access to and removal of blood remnants. For example, after the placenta is recovered, blood clots can form or accumulate inside and on the surfaces of the amnion, intermediate layer, and chorion. Because transmission of blood-borne infectious diseases is a risk associated with tissue transplantation, removal of blood remnants is an important safety consideration when processing placental membrane grafts.

When the amnion and chorion are separated, the intermediate layer or the reticular layer of the chorion are exposed, risking loss of important membrane components during subsequent processing steps. Even gentle rinsing or cleansing of separated amnion or separated chorion may result in removal of important tissue regeneration and wound healing components, including growth factors, cytokines, other regulatory factors, and extracellular matrix molecules.

A separated amnion graft is thin and can result in difficulties when positioning the graft during transplantation. Such a separated amnion graft may have a tendency to roll up on itself during transplantation or may be difficult to secure in place with sutures. It is understood that one or more additional separated amnion or separated chorion sheets may be layered on top of a separated amnion graft during processing to reinforce the graft, to improve its handling during transplantation, and to increase longevity of the graft post-transplantation.

A method of preparing a graft such that the amnion and chorion are not separated may be advantageous. Accordingly, a method of preparing a composition comprising an unseparated amnion/chorion sheet according to the methods of the present invention may be advantageous. For example, washing an unseparated amnion/chorion sheet according to the methods described herein may provide for more efficient removal of blood remnants, including from the inner layers of the sheet. Other potential benefits of washing unseparated amnion/chorion according to the present invention may be increased retention of tissue regeneration and wound healing components or increased preservation of the structure and integrity of the layers compared to processing placental tissue after separating the amnion and chorion. In addition, unseparated amnion/chorion may have increased thickness and improved handling characteristics compared to separated amnion and chorion.

Moreover, preserving unseparated amnion/chorion according to the methods described herein may result in a product with unique properties. For example, dehydrating unseparated amnion/chorion may allow the tissue or certain layers of the tissue (e.g., the compact layer of the amnion, the fibroblast layer of the amnion, the intermediate layer, or the reticular layer of the chorion) to absorb fluids more readily and swell. In addition, dehydrated unseparated amnion/chorion may appear sponge-like or have increased thickness compared to grafts that were not dehydrated during processing. Those unique properties may result in better handling of the graft during transplant or improved healing capacity.

In some embodiments, the disclosure provides a dehydrated unseparated amnion/chorion sheet.

In some embodiments, the disclosure provides an unseparated amnion/chorion sheet substantially free of blood remnants. In some embodiments, the disclosure provides a composition comprising at least one unseparated amnion/chorion sheet, wherein the at least one unseparated amnion/chorion sheet is substantially free of blood remnants. In some embodiments, the unseparated amnion/chorion sheet comprises an intermediate layer. In some embodiments, the unseparated amnion/chorion sheet or the composition is dehydrated.

In some embodiments, the epithelial layer of the amnion is partially removed or substantially removed from the unseparated amnion/chorion sheet. In some embodiments, the sheet comprises a perforation. In some embodiments, the perforation traverses at least one layer of the unseparated amnion/chorion sheet selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

In some embodiments, the composition comprises one or more additional sheets, wherein the one or more additional sheets is selected from a perforated, unseparated amnion/chorion sheet; an unperforated, unseparated amnion/chorion sheet; a perforated, separated amnion sheet; an unperforated, separated amnion sheet; a perforated, separated chorion sheet; and an unperforated, separated chorion sheet. In some embodiments, the unseparated amnion/chorion sheet or the composition is derived from a human placenta.

In some embodiments, the unseparated amnion/chorion sheet or the composition is dehydrated, cryopreserved, or frozen. In some embodiments, the unseparated amnion/chorion sheet or the composition is dehydrated by lyophilization, heat-drying, oven-drying, air-drying, or chemical dehydration. In some embodiments, the at least one unseparated amnion/chorion sheet or the composition is dehydrated by lyophilization.

In some embodiments, the unseparated amnion/chorion sheet or the composition is sterile.

In some embodiments, the unseparated amnion/chorion sheet or the composition comprises a marking. In some embodiments, the marking is selected from an embossment, a stain, a tint, a stamp, and a cut. In some embodiments, the unseparated amnion/chorion sheet or the composition comprises a dye. In some embodiments, the dye is a selected from a natural dye, a vegetable dye, a hypoallergenic dye, and beet juice.

In some embodiments, the unseparated amnion/chorion sheet or the composition has a hemoglobin content of less than a value, of greater than a value of, of at least a value, of a value, or ranging from any two values, wherein the value is selected from about 13 ng/mg, about 12 ng/mg, about 11 ng/mg, about 10 ng/mg, about 9 ng/mg, about 8 ng/mg, about 7 ng/mg, about 6 ng/mg, about 5 ng/mg, about 4 ng/mg, about 3 ng/mg, about 2 ng/mg, about 1 ng/mg, about 0.9 ng/mg, about 0.8 ng/mg, about 0.7 ng/mg, about 0.6 ng/mg, about 0.5 ng/mg, about 0.4 ng/mg, about 0.3 ng/mg, about 0.2 ng/mg, about 0.1 ng/mg, about 0.09 ng/mg, about 0.08 ng/mg, about 0.07 ng/mg, about 0.06 ng/mg, about 0.05 ng/mg, about 0.04 ng/mg, about 0.03 ng/mg, about 0.02 ng/mg, and about 0.01 ng/mg.

In some embodiments, the unseparated amnion/chorion sheet or the composition has a dry mass of less than a value, of greater than a value, of at least a value, of a value, or ranging from any two values, wherein the value is selected from about 1 $mg/cm^2$, about 2 $mg/cm^2$, about 3 $mg/cm^2$, about 4 $mg/cm^2$, about 5 $mg/cm^2$, about 6 $mg/cm^2$, about 7 $mg/cm^2$, about 8 $mg/cm^2$, about 9 $mg/cm^2$, about 10 $mg/cm^2$, about 11 $mg/cm^2$, about 12 $mg/cm^2$, about 13 $mg/cm^2$, about 14 $mg/cm^2$, about 15 $mg/cm^2$, about 16 $mg/cm^2$, about 17 $mg/cm^2$, about 18 $mg/cm^2$, about 19 $mg/cm^2$, about 20 $mg/cm^2$, about 21 $mg/cm^2$, about 22 $mg/cm^2$, about 23 $mg/cm^2$, about 24 $mg/cm^2$, and about 25 $mg/cm^2$.

In some embodiments, the unseparated amnion/chorion sheet or the composition has a water absorption potential of less than a value, of greater than a value, of at least a value, of a value, or ranging from any two values, wherein the value is selected from about 1 $mg/cm^2$, about 2 $mg/cm^2$, about 3 $mg/cm^2$, about 4 $mg/cm^2$, about 5 $mg/cm^2$, about 6 $mg/cm^2$, about 7 $mg/cm^2$, about 8 $mg/cm^2$, about 9 $mg/cm^2$, about 10 $mg/cm^2$, about 11 $mg/cm^2$, about 12 $mg/cm^2$, about 13 $mg/cm^2$, about 14 $mg/cm^2$, about 15 $mg/cm^2$, about 16 $mg/cm^2$, about 17 $mg/cm^2$, about 18 $mg/cm^2$, about 19 $mg/cm^2$, about 20 $mg/cm^2$, about 21 $mg/cm^2$, about 22 $mg/cm^2$, about 23 $mg/cm^2$, about 24 $mg/cm^2$, about 25 $mg/cm^2$, about 26 $mg/cm^2$, about 27 $mg/cm^2$, about 28 $mg/cm^2$, about 29 $mg/cm^2$, about 30 $mg/cm^2$, about 31 $mg/cm^2$, about 32 $mg/cm^2$, about 33 $mg/cm^2$, about 34 $mg/cm^2$, about 35 $mg/cm^2$, about 36 $mg/cm^2$, about 37 $mg/cm^2$, about 38 $mg/cm^2$, about 39 $mg/cm^2$, and about 40 $mg/cm^2$.

In some embodiments, the unseparated amnion/chorion sheet or the composition has a total protein content of less than a value, of greater than a value, of at least a value, of a value, or ranging from any two values, wherein the value is selected from about 25 $\mu g/cm^2$, about 50 $\mu g/cm^2$, about 75 $\mu g/cm^2$, about 100 $\mu g/cm^2$, about 125 $\mu g/cm^2$, about 150 $\mu g/cm^2$, about 175 $\mu g/cm^2$, about 200 $\mu g/cm^2$, about 225 $\mu g/cm^2$, about 250 $\mu g/cm^2$, about 275 $\mu g/cm^2$, about 300 $\mu g/cm^2$, about 325 $\mu g/cm^2$, about 350 $\mu g/cm^2$, about 375 $\mu g/cm^2$, about 400 $\mu g/cm^2$, about 425 $\mu g/cm^2$, about 450 $\mu g/cm^2$, about 475 $\mu g/cm^2$, about 500 $\mu g/cm^2$, about 525 $\mu g/cm^2$, about 550 $\mu g/cm^2$, about 575 $\mu g/cm^2$, about 600 $\mu g/cm^2$, about 625 $\mu g/cm^2$, about 650 $\mu g/cm^2$, about 675 $\mu g/cm^2$, about 700 $\mu g/cm^2$, about 725 $\mu g/cm^2$, about 750 $\mu g/cm^2$, about 775 $\mu g/cm^2$, about 800 $\mu g/cm^2$, about 825 $\mu g/cm^2$, about 850 $\mu g/cm^2$, about 875 $\mu g/cm^2$, about 900 $\mu g/cm^2$, about 925 $\mu g/cm^2$, about 950 $\mu g/cm^2$, about 975 $\mu g/cm^2$, about 1000 $\mu g/cm^2$, about 1025 $\mu g/cm^2$, about 1050 $\mu g/cm^2$, about 1075 $\mu g/cm^2$, about 1100 $\mu g/cm^2$, about 1125 $\mu g/cm^2$, about 1150 $\mu g/cm^2$, about 1175 $\mu g/cm^2$, about 1200 $\mu g/cm^2$, about 1225 $\mu g/cm^2$, about 1250 $\mu g/cm^2$, about 1275 $\mu g/cm^2$, about 1300 $\mu g/cm^2$, about 1325 $\mu g/cm^2$, about 1350 $\mu g/cm^2$, about 1375 $\mu g/cm^2$, about 1400 $\mu g/cm^2$, about 1425 $\mu g/cm^2$, about 1450 $\mu g/cm^2$, about 1475 $\mu g/cm^2$, about 1500 $\mu g/cm^2$, about 1525 $\mu g/cm^2$, about 1550 $\mu g/cm^2$, about 1575 $\mu g/cm^2$, about 1600 $\mu g/cm^2$, about 1625 $\mu g/cm^2$, about 1650 $\mu g/cm^2$, about 1675 $\mu g/cm^2$, about 1700 $\mu g/cm^2$, about 1725 $\mu g/cm^2$, about 1750 $\mu g/cm^2$, about 1775 $\mu g/cm^2$, about 1800 $\mu g/cm^2$, about 1825 $\mu g/cm^2$, about 1850 $\mu g/cm^2$, about 1875 $\mu g/cm^2$, about 1900 $\mu g/cm^2$, about 1925 $\mu g/cm^2$, about 1950 $\mu g/cm^2$, about 1975 $\mu g/cm^2$, and about 2000 $\mu g/cm^2$.

The unseparated amnion/chorion sheet or the composition has a total protein content of less than a value, of greater than a value, of at least a value, of a value, or ranging from any two values, wherein the value is selected from about 0.1 $mg/cm^2$, about 0.2 $mg/cm^2$, about 0.3 $mg/cm^2$, about 0.4 $mg/cm^2$, about 0.5 $mg/cm^2$, about 0.6 $mg/cm^2$, about 0.7 $mg/cm^2$, about 0.8 $mg/cm^2$, about 0.9 $mg/cm^2$, about 1.0 $mg/cm^2$, about 1.1 $mg/cm^2$, about 1.2 $mg/cm^2$, about 1.3 mg/cm², about 1.4 mg/cm², about 1.5 mg/cm², about 1.6 mg/cm², about 1.7 mg/cm², about 1.8 mg/cm², about 1.9 mg/cm², and about 2.0 mg/cm².

In some embodiments, the unseparated amnion/chorion sheet or the composition has a mean thickness of less than a value, of greater than a value, of at least a value, of a value, or ranging from any two values, wherein the value is selected from about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm, about 390 µm, about 400 µm, about 410 µm, about 420 µm, about 430 µm, about 440 µm, about 450 µm, about 460 µm, about 470 µm, about 480 µm, about 490 µm, about 500 µm, about 510 µm, about 520 µm, about 530 µm, about 540 µm, about 550 µm, about 560 µm, about 570 µm, about 580 µm, about 590 µm, about 600 µm, about 700 µm, about 710 µm, about 720 µm, about 730 µm, about 740 µm, about 750 µm, about 760 µm, about 770 µm, about 780 µm, about 790 µm, about 800 µm, about 810 µm, about 820 µm, about 830 µm, about 840 µm, about 850 µm, about 860 µm, about 870 µm, about 880 µm, about 890 µm, about 900 µm, about 910 µm, about 920 µm, about 930 µm, about 940 µm, about 950 µm, about 960 µm, about 970 µm, about 980 µm, about 990 µm, about 1000 µm (about 1 mm), about 1100 µm, about 1200 µm, about 1300 µm, about 1400 µm, about 1500 µm, about 1600 µm, about 1700 µm, about 1800 µm, about 1900 and about 2000 µm (about 2 mm).

In some embodiments, the sheet comprises an intermediate layer having a mean thickness of less than a value, of at least a value, of greater than a value, of a value, or ranging from any two values, wherein the value is selected from about 1 µm, about 2 µm, about 3 µm, about 4 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 80 µm, about 90 µm, about 100 µm, about 110 µm, about 120 µm, about, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm, about 390 µm, about 400 µm, about 410 µm, about 420 µm, about 430 µm, about 440 µm, about 450 µm, about 460 µm, about 470 µm, about 480 µm, about 490 µm, about 500 µm, about 510 µm, about 520 µm, about 530 µm, about 540 µm, about 550 µm, about 560 µm, about 570 µm, about 580 µm, about 590 µm, and about 600 µm.

In some embodiments, the unseparated amnion/chorion sheet or the composition has a surface area of less than a value, of greater than a value, of at least a value, of a value, or ranging from any two values, wherein the value is selected from about 1 mm², about 2 mm², about 3 mm², about 4 mm², about 5 mm², about 6 mm², about 7 mm², about 8 mm², about 9 mm², about 10 mm² (or about 1 cm²), about 2 cm², about 3 cm², about 4 cm², about 5 cm², about 6 cm², about 7 cm², about 8 cm², about 9 cm², about 10 cm², about 11 cm², about 12 cm², about 13 cm², about 14 cm², about 15 cm², about 16 cm², about 17 cm², about 18 cm², about 19 cm², about 20 cm², about 30 cm², about 40 cm², about 50 cm², about 60 cm², about 70 cm², about 80 cm², about 90 cm², about 100 cm², about 10 dm², about 20 dm², about 30 dm², about 40 dm², and about 40 dm².

In some embodiments, the disclosure provides a product prepared by powderizing a sheet or composition disclosed herein.

In some embodiments, the disclosure provides a method of preparing a composition comprising dehydrating an unseparated amnion/chorion. In some embodiments, the disclosure provides a method of preparing a composition comprising removing substantially all blood remnants from an unseparated amnion/chorion.

In some embodiments, the sheet comprises an intermediate layer.

In some embodiments, the method further comprises perforating the unseparated amnion/chorion. In some embodiments, the perforating comprises making one or more holes that traverse at least one layer of the unseparated amnion/chorion selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

In some embodiments, the method comprises washing the unseparated amnion/chorion with at least one suitable washing medium.

In some embodiments, the washing is under vacuum, under pressure, by agitating, or by soaking. In some embodiments, the agitating is performed using a rocker, shaker, stir plate, or rotating mixer. In some embodiments, the method comprises at least one washing step, at least two washing steps, at least three washing steps, at least four washing steps, at least five washing steps, at least six washing steps, at least seven washing steps, at least eight washing steps, at least nine washing steps, at least ten washing steps, or ten or more washing steps, and wherein at least one washing step comprises washing the unseparated amnion/chorion with at least one suitable washing medium. In some embodiments, at least one washing step comprises exchanging the at least one washing medium at least once, once, at least twice, twice, at least thrice, thrice, at least four times, four times, at least five times, five times, at least six times, six times, at least seven times, seven times, at least eight times, eight times, at least nine times, nine times, at least ten times, ten times, or ten or more times. In some embodiments, the exchanging comprises transferring the unseparated amnion/chorion to the at least one washing medium or transferring the at least one washing medium to a container comprising the unseparated amnion/chorion.

In some embodiments, the at least one washing step comprises heating or cooling the tissue, the sheet, or the at least one suitable washing medium. In some embodiments, the heating or cooling comprises placing the unseparated amnion/chorion or the at least one suitable washing medium in an environment having a temperature above, at, or below a refrigeration temperature, a room temperature, or a heated temperature. In some embodiments, the heating or cooling comprises placing the unseparated amnion/chorion or the at least one suitable washing medium in an environment, wherein the environment has less than a temperature of, greater than a temperature of, at least a temperature of, a temperature of, or a range of any two temperatures, wherein the temperature is selected from about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., and about 50° C.

In some embodiments, the unseparated amnion/chorion or the at least one suitable washing medium is placed in an environment for less than a period of time, greater than a period of time, at least a period of time, a period of time, or a range of any two periods of time, wherein the period of time is selected from about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 18 hours, about 24 hours, about 36 hours, about 48 hours, about 64 hours, and about 72 hours. In some embodiments, the temperature of the environment changes over time. In some embodiments, the temperature of environment does not change over time.

In some embodiments, the at least one suitable washing medium is selected from water, a sodium chloride solution, a sodium hypochlorite solution, a hydrogen peroxide solution, Lactated Ringer's solution, Ringer's solution, phosphate-buffered saline (PBS), tris-buffered saline (TBS), Hank's balanced salt solution (HBSS), Dulbecco's phosphate-buffered saline (DPBS), Earle's balanced salt solution (EBSS), standard saline citrate (SSC), HEPES-buffered saline (HBS), Gey's balanced salt solution (GBSS), and a cell culture medium. In some embodiments, the sodium chloride solution is a solution containing a w/v concentration of NaCl of less than a value, of greater than a value, of at least a value, a value, or a range of any two values, wherein the value is selected from about 0.45%, about 0.9%, about 1.8%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 34%, about 35%, and about 36%. In some embodiments, the sodium chloride solution comprises one or more ingredients selected from phosphate, potassium, magnesium, calcium, dextrose, glucose, citrate, lactate, tris, and HEPES. In some embodiments, the cell culture medium is Delbecco's Modified Eagle Medium (DMEM) or Minimum Essential Media (MEM).

In some embodiments, the method comprises pretreating the tissue or the sheet before perforating, before washing, or between any two washing steps. In some embodiments, the pretreating comprises picking material away from the tissue or sheet, or dabbing, rubbing, or massaging the tissue or sheet.

In some embodiments, the method comprises layering on a surface of the unseparated amnion/chorion at least one separated amnion sheet, at least one perforated, separated amnion sheet, at least one unperforated, separated amnion sheet, at least one separated chorion sheet, at least one perforated, separated chorion sheet, at least one unperforated, separated chorion sheet, or at least one perforated, unseparated amnion/chorion sheet.

In some embodiments, the method comprises marking the unseparated amnion/chorion. In some embodiments, the marking is embossing, staining, tinting, stamping, or cutting the unseparated amnion/chorion. In some embodiments, the method comprises marking the unseparated amnion/chorion with a dye. In some embodiments, the dye is a selected from a natural dye, a vegetable dye, a hypoallergenic dye, and beet juice.

In some embodiments, the method comprises preserving the unseparated amnion/chorion. In some embodiments, the preserving comprises dehydrating, cryopreserving, or freezing the unseparated amnion/chorion. In some embodiments, the dehydrating comprises lyophilizing, heat-drying, oven-drying, air-drying, and or chemically dehydrating the unseparated amnion/chorion.

In some embodiments, the method comprises cutting the unseparated amnion/chorion into one or more sheets or cutting an unseparated amnion/chorion sheet into a plurality of sheets.

In some embodiments, the method comprises sterilizing the unseparated amnion/chorion. In some embodiments, the method comprises sterilizing the unseparated amnion/chorion by exposure to gamma radiation, E-beam radiation, ethylene oxide with a stabilizing gas (such as carbon dioxide or hydrochlorofluorocarbons (HCFC)), peracetic acid, hydrogen peroxide gas plasma, or ozone.

In some embodiments, the disclosure provides a composition produced according to a method disclosed herein.

In some embodiments, the disclosure provides a method of healing a wound of a subject comprising applying a sheet, composition, or product disclosed herein to the wound of the subject. In some embodiments, the disclosure provides a use of a sheet, composition, or product disclosed herein for healing a wound of a subject.

In some embodiments, the wound is a wound of the eye, a wound of the skin, a wound of a nerve, a wound of a tendon, a wound of the dura. In some embodiments, the eye wound is a burn, a laceration, a corneal ulceration, a conjunctival lesion, or a surgical wound. In some embodiments, the skin wound is a burn, a laceration, a diabetic ulcer, a venous ulcer, an arterial ulcer, a decubitus ulcer, or a surgical wound. In some embodiments, the composition is applied so that the amnion side of the unseparated amnion/chorion sheet, the chorion side of the unseparated amnion/chorion sheet, the epithelial layer of the amnion, the basement membrane of the amnion, or the trophoblast layer of the chorion faces the wound.

DETAILED DESCRIPTION OF CERTAIN EMBODIMENTS

As used herein, the term "about" refers to a numeric value, including, for example, whole numbers, fractions, and percentages, whether or not explicitly indicated. The term "about" generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

As used herein, "a" or "an" means "at least one" or "one or more" unless specified otherwise. As used herein, the term "or" means "and/or" unless specified otherwise. In the context of a multiple dependent claim, the use of "or" when referring back to other claims refers to those claims in the alternative only.

A. Exemplary Embodiments of Products Made from the Amnion, Intermediate Layer, and Chorion The amnion, intermediate layer, and chorion are composed of numerous components, including cells, growth factors, extracellular matrix molecules, and other biomolecules important for tissue regeneration and wound healing. For example, the amnion, intermediate layer, or chorion may contain cells, such as epithelial cells, fibroblasts, and trophoblasts; growth factors, such as fibroblast growth factors, epidermal growth factor, transforming growth factor (TGF) beta, platelet-derived growth factors, etc.; extracellular matrix molecules such as collagens, elastins, proteoglycans, non-proteoglycan polysaccharides, fibronectins, laminins, nidogens, etc.; and other biomolecules, such as cytokines (e.g., interleukins, TGF-beta, etc.), metalloproteinases, tissue inhibitors of metalloproteinases (TIMPs), etc.

The amnion consists of four layers: an epithelial monolayer, a basement membrane, a compact layer, and a fibroblast layer. The epithelial layer of the amnion is composed of a single layer of epithelial cells arranged on the basement membrane Amniotic epithelial cells may include amniotic stem cells or have stem cell-like characteristics. For example, the cells of the epithelial layer of the amnion may be capable of differentiating into or producing, in the presence of a differentiation-inducing factor, at least one different cell lineage, such as osteogenic, adipogenic, chondrogenic, myogenic, neurogenic, epithelial, or other cell lineage. Amniotic stem cells or cells with stem cell-like characteristics may also be found in other layers of the amnion or chorion.

Amniotic epithelial cells may lack HLA-A, HLA-B (Class IA) and HA-DR (Class II) on their surfaces suggesting that these cells may be immunologically inert and have reduced risk of rejection or immune reaction upon transplantation.

The amnion/chorion may be processed such that the epithelial layer of the amnion is maintained (intact), partially removed, or substantially removed. The epithelial layer may be removed, for example, by using a mechanical procedure or detergent-based procedure. In one embodiment, the epithelial cells are gently scraped away using a cell scraper with the aid of a microscope. In other embodiments, the epithelial layer is removed using an ionic detergent, a nonionic detergent, or a zwitterionic detergent. In yet a further embodiment, after removal of the epithelial layer, the other layers of the amnion/chorion are retained. As used herein, "partially removed" refers to a percentage of the epithelial layer having been removed in the range of about 1% to about 89% and "substantially removed" refers to a percentage of the epithelial layer having been removed in the range of about 90% to about 99%. In some embodiments, at least about 10%, at least about 20%, at least about 30%, at least about 40%, at least about 50%, at least about 60%, at least about 70%, at least about 80%, or at least about 90% of the epithelial layer is removed.

The base of the epithelial cell layer is in contact with the basement membrane of the amnion. The basement membrane of the amnion is a thin layer comprising extracellular matrix components, including collagen types III, IV, and V, noncollagenous glycoproteins (e.g., laminins, fibronectins, and nidogens), and proteoglycans (e.g., perlecans). The compact layer of the amnion is a dense, fibrous network comprising extracellular matrix components, including collagens (e.g., collagen types I, III, V, and VI) and fibronectins, and is almost devoid of cells. The fibroblast layer is the thickest layer of the amnion and comprises fibroblasts and extracellular matrix components, such as collagens (e.g., collagen types I, III, and VI) and noncollagenous glycoproteins (e.g., laminins, fibronectins, and nidogens).

The intermediate layer, or spongy layer, is the interface between the amnion and the chorion. The intermediate layer comprises extracellular matrix components, such as collagens (e.g., collagen types I, III, and IV), proteoglycans, and glycoproteins. In some embodiments, "intermediate layer" includes cells or extracellular matrix derived from an intermediate layer. For example, in some embodiments, when an amnion and a chorion are separated along an intermediate layer, the cells or extracellular matrix derived from the intermediate layer may remain associated with the fibroblast layer of the amnion or may remain associated with the reticular layer of the chorion.

The chorion is several times thicker than the amnion and is composed of three layers: a reticular layer, a basement membrane, and a trophoblast layer. The reticular layer is in contact with the intermediate layer and comprises extracellular components, such as collagens (e.g., collagen types I, III, IV, V, and VI) and proteoglycans. The basement membrane is between the reticular layer and trophoblast layer of the chorion. Components of the basement membrane of the chorion comprise collagens (e.g., collagen type IV), laminins, and fibronectins. The trophoblast layer comprises several layers of trophoblasts and is in contact with the maternal endometrium. As used herein, the term "trophoblast layer" includes cells, extracellular matrix, or blood vessels that may be present and that are derived from the capsular decidua, the portion of the maternal endometrium facing the uterine cavity.

B. Exemplary Embodiments for Collecting and Evaluating Donor Placenta

Placenta may be collected from a human or other mammal, including but not limited to a primate, artiodactyl, perissodactyl, cow, bison, horse, pig, goat, or the like. Placenta may be recovered from a human during a full-term or near full-term Cesarean (C-section) birth. Potential donor mothers may be screened for risk factors to determine whether the placenta is safe and suitable for donation or processing. In one embodiment, a donor mother is tested for one or more viruses or bacteria using serological tests, which can include without limitation antibody, nucleic acid, or culture testing. The viral or bacterial screen may include screening for the human immunodeficiency virus type 1 or type 2 (HIV-1 and HIV-2), the hepatitis B virus (HBV), the hepatitis C virus (HCV), human T-lymphotropic virus type I or type II (HTLV-I and HTLV-II), CMV, or *Treponema pallidum* (a bacterium that causes syphilis). The placenta of a donor mother may be considered acceptable based on review of her health information or any screening test results.

A donor placenta may be recovered during an elective C-section procedure performed in a sterile operating room environment. A recovered placenta may be placed in a labeled, sterile container or bag and submerged in a suitable storage medium. For example, a suitable storage medium includes a sodium chloride solution, such as a solution containing a w/v concentration of NaCl of about 0.45%, about 0.9%, about 1.8%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, or at a w/v concentration of NaCl less than any of the concentrations listed above, greater than any of the concentrations listed above, of at least any of the concentrations listed above, or a range bounded by any two of the concentrations listed above, such as about 0.45% to about 5%, about 5% to about 10%, about 10% to about 20%, about 20% to about 30%, about 20% to about 25%, about 25% to about 30%, about 30% to about 36%, about 0.45% to about 15%, about 15% to about 33%, or about 15% to about 36%.

In addition, a suitable storage medium includes a sodium chloride solution as described above that also contains one or more other ingredients, such as phosphate, potassium, magnesium, calcium, dextrose, glucose, citrate, lactate, tris, HEPES, etc. In some embodiments, the suitable storage medium comprises a buffer. Other suitable storage mediums include water (e.g., purified water, sterile water, or water for injection), Lactated Ringer's solution, Ringer's solution, phosphate-buffered saline (PBS), tris-buffered saline (TBS), Hank's balanced salt solution (HBSS), Dulbecco's phosphate-buffered saline (DPBS), Earle's balanced salt solution (EBSS), standard saline citrate (SSC), HEPES-buffered saline (HBS), Gey's balanced salt solution (GBSS), cell culture mediums (e.g., Delbecco's Modified Eagle Medium (DMEM), Minimum Essential Media (MEM), etc.), or other medium suitable for storing tissue.

The container or bag may be shipped on wet ice to a processing laboratory for processing and evaluation. If the donor mother's health information and screening tests are satisfactory (i.e., indicate no risk or acceptable level of risk to human handling or use), the donor placenta may be processed for human medical applications.

After opening the shipment at the processing laboratory, personnel may verify that the sterile container or bag is still sealed and in coolant, and that the donor number on the accompanying paperwork matches the number on the sterile container. Processing of donor placenta for human medical applications may be conducted in a controlled, aseptic environment, such as in a hood or clean room.

C. Exemplary Embodiments for Dissecting or Cutting

A placenta may be processed by dissecting the unseparated amnion/chorion from the placental disc and umbilical cord. As used herein, "unseparated amnion/chorion" and "unseparated amnion/chorion tissue" are used interchangeably throughout to refer to the membrane portion of a placenta, irrespective of whether the membrane portion is attached to or detached from the placental disc and umbilical cord. An unseparated amnion/chorion may include an intermediate layer or may not include an intermediate layer, the inclusion or exclusion of which may depend on the characteristics of the donor placenta. In addition, unseparated amnion/chorion, as used herein, includes unseparated amnion/chorion processed by any step or any combination of steps selected from dissecting, cutting, perforating, washing, sterilizing, and preserving. An unseparated amnion/chorion, as used herein, includes unseparated amnion/chorion having an epithelial layer of amnion (also referred to as intact) and unseparated amnion/chorion in which the epithelial layer of the amnion has been partially removed or substantially removed.

Amnion and chorion may be separated before, during, or after any step or combination of steps selected from dissecting, cutting, perforating, and washing. Amnion and chorion may be separated by any method understood by a person of ordinary skill in the art, including, but not limited to, gently separating the amnion and chorion by hand. As used herein, "separated amnion" and "separated amnion tissue" interchangeably refer to amnion that has been separated from chorion. A separated amnion may include an intermediate layer or may not include an intermediate layer. For example, in some embodiments, the intermediate layer is substantially intact on the separated amnion. As used herein, "separated chorion" and "separated chorion tissue," interchangeably refer to chorion that has been separated from amnion. A separated chorion may include an intermediate layer or may not include an intermediate layer. For example, in some embodiments, the intermediate layer is substantially intact on the separated chorion. As used herein, an intermediate layer that is substantially intact may include an intermediate layer that appears to the naked eye to cover the separated amnion or the separated chorion without visible holes. For example, the separated amnion or the separated chorion may lack intermediate layer at the periphery of the tissue. An intermediate layer that is substantially intact may also include an intermediate layer that appears to the naked eye to cover at least about 60%, at least about 65%, at least about 70%, at least about 75%, at least about 80%, at least about 85%, at least about 90%, or at least about 95% of the separated amnion or the separated chorion.

An unseparated amnion/chorion may be dissected away from the placental disc and umbilical cord or cut using any number of methods known to those of ordinary skill in the art, for example by using a scalpel, a pair of surgical scissors, a rotary blade, etc. In one embodiment, a placenta may be transferred to a surface suitable for dissection, such as a soft, nonporous mat, and the unseparated amnion/chorion dissected away from the rest of the placenta, e.g., using surgical scissors or a scalpel.

An unseparated amnion/chorion, a separated amnion, or a separated chorion may be cut into one or more sheets before, during, or after any step or any combination of steps selected from dissecting, perforating, washing, sterilizing, and preserving. For example, an unseparated amnion/chorion, a separated amnion, or a separated chorion may be cut into 1 sheet, 2 sheets, 3 sheets, 4 sheets, 5 sheets, 6 sheets, 7 sheets, 8 sheets, 9 sheets, 10 sheets, 11 sheets, 12 sheets, 13 sheets, 14 sheets, 15 sheets, 16 sheets, 17 sheets, 18 sheets, 19 sheets, 20 sheets, or less than any number of sheets listed above, greater than any number of sheets listed above, at least any number of sheets listed above, or a range of sheets bounded by any two numbers listed above. In addition, in other embodiments, an unseparated amnion/chorion sheet, a separated amnion sheet, or a separated chorion sheet may be cut into one or more additional sheets before, during, or after any step or any combination of steps selected from dissecting, perforating, washing, sterilizing, and preserving. As used herein, "sheet" includes any three-dimensional conformation that may be formed from the sheet, including but not limited to, a cylindrical shape (e.g., sleeve), a cone shape, etc.

An unseparated amnion/chorion, a separated amnion, or a separated chorion may be cut to any shape or size sheet that the tissue may accommodate. For example, the tissue may be cut to or may have a regular or irregular shape. In some embodiments, the tissue may be cut to or may have the shape of a square, rectangle, oval, or circle, etc. In other embodiments, the tissue may be cut to have or may have one or more straight or curved edges.

An unseparated amnion/chorion, a separated amnion, or a separated chorion may be cut to or may have any diameter that the tissue may accommodate, such as a diameter of about 1 mm, about 2 mm, about 3 mm, about 4 mm, about 5 mm, about 6 mm, about 7 mm, about 8 mm, about 9 mm, about 10 mm (or about 1 cm), about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, or less than any value listed above, greater than any value listed above, at least any value listed above, or a range of values bounded by any two of the values listed above, such as about 1 mm to about 5 mm, about 1 cm to about 5 cm, about 10 cm to about 15 cm, about 1 mm to about 20 cm, about 1 mm to about 10 mm, about 10 mm to about 10 cm, about 10 cm to about 20 cm.

In addition, unseparated amnion/chorion, a separated amnion, or a separated chorion may be cut to or may have any length or width that the tissue may accommodate, such as a length or width of about 1 mm, about 2 mm, about 3 mm, about 4 mm, about 5 mm, about 6 mm, about 7 mm, about 8 mm, about 9 mm, about 10 mm (or about 1 cm), about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, or less than any value listed above, greater than any value listed above, at least any value listed above, or a range of values bounded by any two of the values listed above, such as about 1 mm to about 5 mm, about 1 cm to about 5 cm, about 10 cm to about 15 cm, about 1 mm to about 20 cm, about 1 mm to about 10 mm, about 10 mm to about 10 cm, about 10 cm to about 20 cm.

Further, unseparated amnion/chorion, a separated amnion, or a separated chorion may be cut to or may have any surface area that the tissue may accommodate, including a surface area of about 1 $mm^2$, about 2 $mm^2$, about 3 $mm^2$, about 4 $mm^2$, about 5 $mm^2$, about 6 $mm^2$, about 7 $mm^2$, about 8 $mm^2$, about 9 $mm^2$, about 10 $mm^2$ (or about 1 $cm^2$), about 2 $cm^2$, about 3 $cm^2$, about 4 $cm^2$, about 5 $cm^2$, about 6 $cm^2$, about 7 $cm^2$, about 8 $cm^2$, about 9 $cm^2$, about 10 $cm^2$, about 11 $cm^2$, about 12 $cm^2$, about 13 $cm^2$, about 14 $cm^2$, about 15 $cm^2$, about 16 $cm^2$, about 17 $cm^2$, about 18 $cm^2$, about 19 $cm^2$, about 20 $cm^2$, about 30 $cm^2$, about 40 $cm^2$, about 50 $cm^2$, about 60 $cm^2$, about 70 $cm^2$, about 80 $cm^2$, about 90 $cm^2$, about 100 $cm^2$ (about 10 $dm^2$), about 20 $dm^2$, about 30 $dm^2$, about 40 $dm^2$, or less than any value listed above, greater than any value listed above, at least any value listed above, or a range of values bounded by any two of the values listed above, such as about 1 $mm^2$ to about 5 $mm^2$, about 1 $cm^2$ to about 5 $cm^2$, about 10 $cm^2$ to about 20 $cm^2$, about 50 $cm^2$ to about 20 $dm^2$, about 1 $mm^2$ to about 10 $mm^2$, about 1 $mm^2$ to about 10 $cm^2$, about 10 $cm^2$ to about 100 $cm^2$, about 40 $cm^2$ to about 40 $dm^2$, or about 1 $mm^2$ to about 40 $dm^2$.

D. Exemplary Embodiments for Perforating

An unseparated amnion/chorion, a separated amnion, or a separated chorion may be perforated before, during, or after any step or any combination of steps selected from dissecting, cutting, washing, sterilizing, and preserving. When used as a verb herein, "perforate," and other forms (e.g., perforated, perforating, etc.) refer to making one or more holes having any shape or pattern. When used as an adjective herein, "perforated" refers to having one or more holes having any shape or pattern. When used as a noun herein, "perforation" refers to one or more holes having any shape or pattern. "Perforate" and any other form of the word as used herein does not refer to a tear or break.

As used herein, "perforate," and other forms (e.g., perforated, perforating, etc.) includes, but is not limited to, perforating by making one or more holes that traverse the entire thickness of one or more membrane(s) or layer(s). In some embodiments, methods of perforating include making one or more holes that traverse the entire thickness of an unseparated amnion/chorion, a separated amnion, or a separated chorion. In other embodiments, methods of perforating an unseparated amnion/chorion, a separated amnion, or a separated chorion include making one or more holes traversing any one layer or combination of layers selected from the epithelial layer of the amnion, the basement membrane of the amnion, the compact layer of the amnion, and the fibroblast layer of the amnion, the intermediate layer, the reticular layer of the chorion, the basement membrane of the chorion, and the trophoblast layer of the chorion. In a further embodiment, a method of perforating an unseparated amnion/chorion or separated amnion includes making one or more holes traversing the epithelial layer of the amnion and the basement membrane of the amnion. In another embodiment, a method of perforating an unseparated amnion/chorion or separated chorion includes making one or more holes traversing the trophoblast layer of the chorion and the basement membrane of the chorion. In further embodiments, methods of perforating an unseparated amnion/chorion, a separated amnion, or a separated chorion includes making one or more holes that do not traverse any one layer or any combination of layers selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

"Perforate," and other forms (e.g., perforated, perforating, etc.) as used herein also includes making one or more holes that partially traverse one or more membrane(s) or layer(s). For example, in some embodiments, methods of perforating an unseparated amnion/chorion or separated amnion include making one or more holes that partially traverse the amnion. In other embodiments, methods of perforating an unseparated amnion/chorion or separated chorion include making one or more holes that partially traverse the chorion. In further embodiments, methods of perforating an unseparated amnion/chorion, a separated amnion, or a separated chorion include making one or more holes that partially traverse any one or any combination of layers selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

"Perforate," and other forms (e.g., perforated, perforating, etc.) as used herein also includes making one or more holes that traverse or partially traverse the one or more membrane(s) or layer(s) across one or more perforations. For example, in some embodiments, methods of perforating an unseparated amnion/chorion, a separated amnion, or a separated chorion include making one or more holes that traverse the entire thickness of the tissue in one portion and one or more holes that partially traverse the tissue in another portion. In other embodiments, methods of perforating an unseparated amnion/chorion include making one or more holes that traverse the amnion and chorion in one portion, and making one or more holes that traverse the amnion and partially traverses the chorion in another portion. In further embodiments, methods of perforating an unseparated amnion/chorion include making one or more holes that traverse the chorion in one portion, and making one or more holes that traverse the chorion and partially traverses the amnion in another portion. In additional embodiments, methods of perforating unseparated amnion/chorion, separated amnion, or separated chorion include making one or more holes that traverse or partially traverse any one or any combination of layers in one portion, and making one or more holes that traverse or partially traverse any one or any combination of layers to a different extent in another portion. The any one or any combination of layers referred to may be selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

As used herein, "perforated" includes, but is not limited to, having one or more holes traversing the entire thickness of one or more membrane(s) or layer(s). For example, in some embodiments, a perforated, unseparated amnion/chorion; a perforated, separated amnion; or a perforated, separated chorion has one or more holes traversing one or more layers of the tissue. In other embodiments, a perforated, unseparated amnion/chorion; a perforated, separated amnion; or a perforated, separated chorion has one or more holes traversing any one layer or combination of layers selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion. In a further embodiment, a perforated, unseparated amnion/chorion or a perforated, separated amnion has one or more holes traversing the epithelial layer of the amnion and the basement membrane of the amnion. In another embodiment, a perforated, unseparated amnion/chorion or a perforated, separated chorion has one or more holes traversing the trophoblast layer of the chorion and the basement membrane of the chorion. In a further embodiment, a perforated, unseparated amnion/chorion; a perforated, separated amnion; or a perforated, separated chorion has one or more holes that do not traverse any one layer or any combination of layers selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

Perforated, as used herein, may also include having one or more holes that partially traverse one or more membrane(s) or layer(s). In some embodiments, a perforated, unseparated amnion/chorion or a perforated, separated amnion has one or more holes that partially traverse the amnion. In other embodiments, a perforated, unseparated amnion/chorion or a perforated separated chorion has one or more holes that partially traverse the chorion. In other embodiments, a perforated, unseparated amnion/chorion; a perforated, separated amnion; or a perforated, separated chorion has one or more holes that partially traverse any one or any combination of layers selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

Perforated, as used herein, may also include having one or more holes that traverse or partially traverse one or more membrane(s) or layer(s) differently across one or more perforations. For example, a perforated, unseparated amnion/chorion; a perforated, separated amnion; or a perforated, separated chorion may have one or more holes that traverse the entire thickness of the tissue in one portion and one or more holes that partially traverse the tissue in another portion. In one embodiment, a perforated, unseparated amnion/chorion has one or more holes that traverse the amnion and chorion in one portion, and has one or more holes that traverse the amnion and partially traverses the chorion in another portion. In another embodiment, a perforated, unseparated amnion/chorion has one or more holes that traverse the chorion in one portion and one or more holes that traverse the chorion and partially traverses the amnion in another portion. In some embodiments, a perforated, unseparated amnion/chorion; a perforated, separated amnion; or a perforated, separated chorion has one or more holes that traverse or partially traverse any one or any combination of layers in one portion and one or more holes that traverse or partially traverse any one or any combination of layers to a different extent in another portion. The any one or any combination of layers referred to herein may be selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

As used herein, "perforation" includes, but is not limited to, one or more holes traversing the entire thickness of one or more membrane(s) or layer(s). For example, a perforation may traverse the entire thickness of an unseparated amnion/chorion, a separated amnion, or a separated chorion. In other embodiments, a perforation may traverse one or more layers of an unseparated amnion/chorion, a separated amnion, or a separated chorion. In one embodiment, a perforation traverses the entire thickness of an unseparated amnion/chorion, a separated amnion, or a separated chorion. In other embodiments, a perforation traverses any one layer or any combination of layers selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion. In a further embodiment, a perforation traverses the epithelial layer and basement membrane of the amnion. In another embodiment, a perforation traverses the trophoblast layer and basement membrane of the chorion. In another embodiment, a perforation does not traverse any one layer or any combination of layers selected from epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

A perforation, as used herein, may also include one or more holes partially traversing one or more membrane(s) or layer(s). In one embodiment, a perforation is one or more holes that partially traverses the amnion. In another embodiment, a perforation is one or more holes that partially traverses the chorion. In some embodiments, a perforation is one or more holes that partially traverses any one or any combination of layers selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

A perforation, as used herein, may also include one or more holes traversing or partially traversing one or more membrane(s) or layer(s) differently across the perforation.

For example, a perforation may have one or more holes that traverse the entire thickness of an unseparated amnion/chorion, a separated amnion, or a separated chorion in one portion and have one or more holes that partially traverse the tissue in another portion. In one embodiment, a perforation traverses the amnion and chorion in one portion, and traverses the amnion and partially traverses the chorion in another portion. In another embodiment, a perforation traverses the chorion in one portion and traverses the chorion and partially traverses the amnion in another portion. In some embodiments, a perforation traverses or partially traverses any one or any combination of layers in one portion and traverses or partially traverses any one or any combination of layers to a different extent in another portion. The any one or any combination of layers referred to herein may be selected from the epithelial layer of the amnion, the basement membrane of the amnion, the compact layer of the amnion, the fibroblast layer of the amnion, the intermediate layer, the reticular layer of the chorion, the basement membrane of the chorion, and the trophoblast layer of the chorion.

As previously stated, "perforation," as used herein, refers to one or more holes having any shape or pattern. As used herein, a "hole" may have any depth ranging from less than a micron to greater than several millimeters. The depth of a hole may be determined by measuring the distance between one opening of the hole to the other opening of the hole. In some embodiments, the depth of a hole may be about 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 25 µm, about 30 µm, about 40 µm, about 50 µm, about 60 µm, about 70 µm, about 80 µm, about 90 µm, about 100 µm (about 0.1 mm), about 0.2 mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm, about 10 mm, or less than any value listed above, greater than any value listed above, at least any value listed above, or a range of values bounded by any two of the values listed above, such as about 1 µm to about 5 µm, about 5 µm to about 10 µm, about 15 µm to about 25 µm, about 50 µm to about 0.1 mm, about 0.1 mm to about 0.5 mm, about 1 mm to about 10 mm, about 1 µm to about 100 µm, about 0.1 mm to about 10 mm, or about 1 µm to about 10 mm.

A hole may have an area ranging from less than a square micron to greater than several square centimeters. The area of a hole may be determined by measuring the area spanning an opening of the hole. In some embodiments, a hole may have an area of about 1 µm$^2$, about 2 µm$^2$, about 3 µm$^2$, about 4 µm$^2$, about 5 µm$^2$, about 6 µm$^2$, about 7 µm$^2$, about 8 µm$^2$, about 9 µm$^2$, about 10 µm$^2$, about 11 µm$^2$, about 12 µm$^2$, about 13 µm$^2$, about 14 µm$^2$, about 15 µm$^2$, about 16 µm$^2$, about 17 µm$^2$, about 18 µm$^2$, about 19 µm$^2$, about 20 µm$^2$, about 25 µm$^2$, about 30 µm$^2$, about 40 µm$^2$, about 50 µm$^2$, about 60 µm$^2$, about 70 µm$^2$, about 80 µm$^2$, about 90 µm$^2$, about 100 µm$^2$ (about 0.1 mm$^2$), about 0.2 mm$^2$, about 0.3 mm$^2$, about 0.4 mm$^2$, about 0.5 mm$^2$, about 0.6 mm$^2$, about 0.7 mm$^2$, about 0.8 mm$^2$, about 0.9 mm$^2$, about 1 mm$^2$, about 2 mm$^2$, about 3 mm$^2$, about 4 mm$^2$, about 5 mm$^2$, about 6 mm$^2$, about 7 mm$^2$, about 8 mm$^2$, about 9 mm$^2$, about 10 mm$^2$ (about 1 cm$^2$), about 2 cm$^2$, about 3 cm$^2$, about 4 cm$^2$, about 5 cm$^2$, about 6 cm$^2$, about 7 cm$^2$, about 8 cm$^2$, about 9 cm$^2$, about 10 cm$^2$, or less than any value listed above, greater than any value listed above, at least any value listed above, or a range of values bounded by any two of the values listed above, such as about 1 µm$^2$ to about 10 µm$^2$, about 10 µm$^2$ to about 100 µm$^2$, about 100 µm$^2$ to about 1 mm$^2$, about 1 mm$^2$ to about 10 mm$^2$, or about 1 cm$^2$ to about 10 cm$^2$, about 1 µm$^2$ to about 100 µm$^2$, about 0.1 mm$^2$ to about 10 mm$^2$, or about 1 µm$^2$ to about 10 cm$^2$.

The distance between any two adjacent holes may range from less than a micron to greater than several millimeters. The distance between any two adjacent holes may be determined by measuring the distance between the two closest points on the boundaries of the respective holes. In some embodiments, two holes may be separated by a distance of about 1 µm, about 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 25 µm, about 30 µm, about 40 µm, about 50 µm, about 60 µm, about 70 µm, about 80 µm, about 90 µm, about 100 µm (about 0.1 mm), about 0.2 mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm, about 10 mm, or less than any value listed above, greater than any value listed above, at least any value listed above, or a range of values bounded by any two of the values listed above, such as about 1 µm to about 10 µm, about 10 µm to about 50 µm, about 50 µm to about 100 µm, about 0.1 mm to about 1 mm, about 1 mm to about 10 mm, about 1 µm to about 10 mm, about 1 µm to about 100 µm, or about 0.1 mm to about 10 mm.

A perforation may comprise a plurality of holes having a total area less than the surface area of the sheet. In some embodiments, the total area of a plurality of holes may be less than the surface area of the sheet by about 1%, by about 2%, by about 3%, by about 4%, by about 5%, by about 6%, by about 7%, by about 8%, by about 9%, by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 42%, by about 43%, by about 44%, by about 45%, by about 46%, by about 47%, by about 48%, by about 49%, by about 50%, or less than any percentage listed above, greater than any percentage listed above, at least any percentage listed above, or a range of percentages bounded by any two of the percentages listed above, such as by about 1% to by about 5%, by about 5% to by about 10%, by about 10% to by about 15%, by about 15% to by about 20%, by about 25% to by about 30%, by about 30% to by about 40%, by about 40% to by about 50%, by about 1% to by about 50%, by about 1% to by about 25%, or by about 25% to by about 50%.

An unseparated amnion/chorion, a separated amnion, or a separated chorion may be perforated using any number of perforators. As used herein, a "perforator" refers to a device that is capable of making a perforation including, but not limited to, a needle, a roller with one or more pins, a stamper with one or more pins, a hole punch, a punch and die, a die cutter (e.g., a rotary die cutter), a drill and bit, a blade, scalpel or other sharp object, a skin graft mesher with blades, high-pressure water or air gun, a laser, etc. A perforating device may have one or multiple penetrators of the same or different type.

A perforator may be used to make perforations that traverse or partially traverse one or more layers or membranes. For example, in some embodiments, a perforator may be applied to the surface of an unseparated amnion/chorion, a separated amnion, or a separated chorion, and a portion of the perforator penetrating the surface (also referred to herein as a "penetrator") permitted to penetrate the entire thickness of the tissue or sheet or to only penetrate to a particular thickness or a particular layer. As used herein, a "penetrator" includes, but is not limited to, a needle, punch, pin, die, bit, blade, laser beam, water stream, or air stream. A penetrator or penetrators may be adapted to penetrate a tissue or sheet to a particular thickness or a particular layer, for example, by adjusting the extent of penetration by controlling the pressure applied to the penetrator(s) or by controlling the length of the penetrator(s). "Air" includes any suitable gas, such as atmospheric air, oxygen, or an inert gas such as nitrogen or argon.

A penetrator or penetrators may be of any length, dimension, or pattern that is capable of making a perforation having any one of the depths or areas, or any one of the ranges of depths or areas, recited above. In some embodiments, the distance between any two adjacent penetrators may be of any distance that is capable of making a perforation having a distance between any two adjacent holes as recited above.

A perforating device may have a penetrator or penetrators capable of making one or more holes having an opening with an area ranging from less than a square micron to greater than several square centimeters. In some embodiments, the penetrator or penetrator(s) are capable of making one or more holes having an area of about 1 $\mu m^2$, about 2 $\mu m^2$, about 3 $\mu m^2$, about 4 $\mu m^2$, about 5 $\mu m^2$, about 6 $\mu m^2$, about 7 $\mu m^2$, about 8 $\mu m^2$, about 9 $\mu m^2$, about 10 $\mu m^2$, about 11 $\mu m^2$, about 12 $\mu m^2$, about 13 $\mu m^2$, about 14 $\mu m^2$, about 15 $\mu m^2$, about 16 $\mu m^2$, about 17 $\mu m^2$, about 18 $\mu m^2$, about 19 $\mu m^2$, about 20 $\mu m^2$, about 25 $\mu m^2$, about 30 $\mu m^2$, about 40 $\mu m^2$, about 50 $\mu m^2$, about 60 $\mu m^2$, about 70 $\mu m^2$, about 80 $\mu m^2$, about 90 $\mu m^2$, about 100 $\mu m^2$ (about 0.1 $mm^2$), about 0.2 $mm^2$, about 0.3 $mm^2$, about 0.4 $mm^2$, about 0.5 $mm^2$, about 0.6 $mm^2$, about 0.7 $mm^2$, about 0.8 $mm^2$, about 0.9 $mm^2$, about 1 $mm^2$, about 2 $mm^2$, about 3 $mm^2$, about 4 $mm^2$, about 5 $mm^2$, about 6 $mm^2$, about 7 $mm^2$, about 8 $mm^2$, about 9 $mm^2$, about 10 $mm^2$ (about 1 $cm^2$), about 2 $cm^2$, about 3 $cm^2$, about 4 $cm^2$, about 5 $cm^2$, about 6 $cm^2$, about 7 $cm^2$, about 8 $cm^2$, about 9 $cm^2$, about 10 $cm^2$, or less than any value listed above, greater than any value listed above, at least any value listed above, or a range of values bounded by any two of the values listed above, such as about 1 $\mu m^2$ to about 10 $\mu m^2$, about 10 $\mu m^2$ to about 100 $\mu m^2$, about 100 $\mu m^2$ to about 1 $mm^2$, about 1 $mm^2$ to about 10 $mm^2$, or about 1 $cm^2$ to about 10 $cm^2$, about 1 $\mu m^2$ to about 100 $\mu m^2$, about 0.1 $mm^2$ to about 10 $mm^2$, or about 1 $\mu m^2$ to about 10 $cmm^2$. A perforating device may have more than one penetrator capable of making holes of the same or different sizes. For example, half of the penetrators of a perforator may be capable of making holes ranging from about 20 $\mu m^2$ to 1 $mm^2$ and the other half of the penetrators may be capable of making holes ranging from about 0.4 $mm^2$ to about 10 $mm^2$.

A perforating device may have a penetrator or penetrators having a length corresponding to the thickness of at least one layer or membrane, or ranging from less than a micron to greater than several millimeters. In some embodiments, the length of a penetrator or penetrators may be about 1 $\mu m$, about 2 $\mu m$, about 3 $\mu m$, about 4 $\mu m$, about 5 $\mu m$, about 6 $\mu m$, about 7 $\mu m$, about 8 $\mu m$, about 9 $\mu m$, about 10 $\mu m$, about 11 $\mu m$, about 12 $\mu m$, about 13 $\mu m$, about 14 $\mu m$, about 15 $\mu m$, about 16 $\mu m$, about 17 $\mu m$, about 18 $\mu m$, about 19 $\mu m$, about 20 $\mu m$, about 25 $\mu m$, about 30 $\mu m$, about 40 $\mu m$, about 50 $\mu m$, about 60 $\mu m$, about 70 $\mu m$, about 80 $\mu m$, about 90 $\mu m$, about 100 $\mu m$ (about 0.1 mm), about 0.2 mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm, about 10 mm, or less than any value listed above, greater than any value listed above, at least any value listed above, or a range of values bounded by any two of the values listed above, such as about 1 $\mu m$ to about 10 $\mu m$, about 10 $\mu m$ to about 50 $\mu m$, about 50 $\mu m$ to about 100 $\mu m$, about 0.1 mm to about 1 mm, about 1 mm to about 10 mm, about 1 $\mu m$ to about 10 mm, about 1 $\mu m$ to about 100 $\mu m$, or about 0.1 mm to about 10 mm. A perforating device may have more than one penetrator of the same or different lengths. For example, half of the penetrators of a perforator may have a length of about 10 $\mu m$ and the other half of the penetrators may have a length of about 1 mm.

Examples of perforating devices that may be used to make perforations that traverse or partially traverse one or more layers or membranes include a rolling device having a cylindrical core and multiple penetrators extending from the core or a stamping device having a platform and multiple penetrators extending from the platform. A rolling device or a stamping device may have a handle. The penetrators of these exemplary perforating devices may be of the same length or of varying lengths. The length of the penetrators may correspond to the desired hole depth, correspond to the thickness of the layer(s) sought to be perforated, or range from less than a micron to greater than several millimeters.

Other examples of perforating devices that may be used to make perforations that traverse or partially traverse one or more layers or membranes include a perforating bed of penetrators. The perforating bed may be made of a rigid or flexible material. The penetrators may have the same length or different lengths or be capable of making holes of the same or different sizes. In one embodiment, a tissue or sheet is placed on a perforating bed and pressure is applied from above. For example, a bladder (e.g., balloon, etc.) may be used to apply pressure to the surface of the tissue or sheet. The pressure applied may be consistent across the perforating bed or may vary from one area of the bed to another. Multiple perforating beds could be used to make perforations originating from both sides of a tissue or sheet.

E. Exemplary Embodiments for Washing or Pretreating

As used herein, "washing" refers to trying to remove material (e.g., blood remnants or other debris) from the surface or interior of an unseparated amnion/chorion, a separated amnion, or a separated chorion in the presence of a suitable washing medium by any number of methods, including but not limited to flushing, immersing, perfusing, soaking, or agitating in the presence or absence of pressure or vacuum. In some embodiments, the agitating is performed using a rocker, shaker, stir plate, rotating mixer, or other equipment capable of agitating. In some embodiments, an unseparated amnion/chorion, a separated amnion, or a separated chorion may be washed before, during, or after any step or any combination of steps selected from dissecting, separating, pretreating, cutting, and perforating. For example, in some embodiments, an unseparated amnion/chorion, a separated amnion, or a separated chorion may be washed before or after being perforated.

As used herein, "pretreating" is one or more steps intended to remove material (e.g., blood remnants or other debris) from the surface or loosen material from the interior of an unseparated amnion/chorion, a separated amnion, or a separated chorion by any number of methods, including but not limited to picking, dabbing, rubbing, or massaging with a fingertip, swab, or gauze. Pretreatment may be performed manually. In some embodiments, the pretreating is performed in the presence of a suitable washing medium. In some embodiments, an unseparated amnion/chorion, a separated amnion, or a separated chorion may be pretreated before, during, or after any step or any combination of steps selected from dissecting, separating, cutting, perforating, and washing. For example, in some embodiments, an unseparated amnion/chorion, a separated amnion, or a separated chorion may be pretreated before or after being perforated.

In some embodiments, the material sought to be removed from the surface or interior of an unseparated amnion/chorion, a separated amnion, or a separated chorion is blood remnants (e.g., blood clots, whole blood, intact blood cells, blood cell remnants, etc.) or other debris. In some embodiments, e.g., following pretreatment or washing, an unseparated amnion/chorion, a separated amnion, or a separated chorion is substantially free of blood remnants. In other embodiments, e.g., following pretreatment or washing, a perforated, unseparated amnion/chorion; a perforated, separated amnion; or a perforated, separated chorion is substantially free of blood remnants. As used herein, "substantially free" refers to a significantly reduced amount of an agent referenced. In some embodiments, the reduction in amount is greater than about 50%. In some embodiments, the reduction in amount is greater than about 60%, 70%, 80%, 90%, or 95%. In some embodiments, substantially free of blood remnants means that the hemoglobin content is less than about 13 ng hemoglobin per mg of the tissue or sheet ("ng/mg"). In some embodiments, substantially free of blood remnants means that the hemoglobin content is less than about 12 ng/mg, about 11 ng/mg, about 10 ng/mg, about 9 ng/mg, about 8 ng/mg, about 7 ng/mg, about 6 ng/mg, about 5 ng/mg, about 4 ng/mg, about 3 ng/mg, about 2 ng/mg, about 1 ng/mg, about 0.9 ng/mg, about 0.8 ng/mg, about 0.7 ng/mg, about 0.6 ng/mg, about 0.5 ng/mg, about 0.4 ng/mg, about 0.3 ng/mg, about 0.2 ng/mg, about 0.1 ng/mg, about 0.09 ng/mg, about 0.08 ng/mg, about 0.07 ng/mg, about 0.06 ng/mg, or about 0.05 ng/mg.

In one embodiment, a suitable washing medium includes a sodium chloride solution, such as a solution containing a w/v concentration of NaCl of about 0.45%, about 0.9%, about 1.8%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 34%, about 35%, about 36%, or less than any percentage listed above, greater than any percentage listed above, at least any percentage listed above, or a range of percentages bounded by any two of the percentages listed above, such as about 0.45% to about 5%, about 5% to about 10%, about 10% to about 20%, about 20% to about 30%, about 20% to about 25%, about 25% to about 30%, about 30% to about 36%, about 0.45% to about 15%, about 15% to about 33%, or about 15% to about 36%.

In addition, a suitable washing medium includes a sodium chloride solution as described above that also contains one or more other ingredients, such as phosphate, potassium, magnesium, calcium, dextrose, glucose, citrate, lactate, tris, HEPES, etc. Other suitable washing mediums include water (e.g., purified or sterile), Lactated Ringer's solution, Ringer's solution, phosphate-buffered saline (PBS), tris-buffered saline (TBS), Hank's balanced salt solution (HBSS), Dulbecco's phosphate-buffered saline (DPBS), Earle's balanced salt solution (EBSS), standard saline citrate (SSC), HEPES-buffered saline (HBS), Gey's balanced salt solution (GBSS), cell culture mediums (e.g., Delbecco's Modified Eagle Medium (DMEM), Minimum Essential Media (MEM), etc.), hydrogen peroxide solutions, sodium hypochloride solutions, or other medium suitable for washing tissue.

A tissue or a sheet may be washed in at least one suitable washing medium over one or more washing steps. For example, a tissue or sheet may be washed in at least one washing step, at least two washing steps, at least three washing steps, at least four washing steps, at least five washing steps, at least six washing steps, at least seven washing steps, at least eight washing steps, at least nine washing steps, at least ten washing steps, or ten or more washing steps.

In some embodiments, at least one washing step includes exchanging the at least one suitable washing medium at least once, once, at least twice, twice, at least thrice, thrice, at least four times, four times, at least five times, five times, at least six times, six times, at least seven times, seven times, at least eight times, eight times, at least nine times, nine times, at least ten times, ten times, or ten or more times. A suitable washing medium may be exchanged by transferring a tissue or a sheet from old medium to fresh medium of the same or different type, or by removing some or all of the old medium and transferring fresh medium of the same or different type.

In other embodiments, at least one washing step includes comprises heating or cooling a tissue, sheet, or suitable washing medium. For example, a tissue, sheet, or suitable washing medium may be placed in an environment having a temperature above, at, or below a refrigeration temperature, a room temperature, or a heated temperature. As used herein, "refrigeration temperature" refers to a temperature of from about 1° C. to about 12° C., "room temperature" refers to a temperature of from about 13° C. to about 25° C., and "heated temperature" refers to a temperature of from about 26° C. to about 50° C.

In some embodiments, a tissue, sheet, or suitable washing medium is placed in an environment having a temperature of about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., or less than any value listed above, greater than any value listed above, at least any value listed above, or a range of values bounded by any two of the values listed above, such as refrigeration temperature, room temperature, or heated temperature.

A tissue, sheet, or suitable washing medium may be placed in any of the environments listed above for any period of time ranging from minutes to hours. For example, the period of time may be about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 48 hours, or less than any value listed above, greater than any value listed above, at least any value listed above, or a range of values bounded by any two of the values listed above, such as about 5 minutes to about 30 minutes, about 30 minutes to about 1 hour, about 1 hour to about 18 hours, about 18 hours to about 36 hours, about 36 hours to about 60 hours, about 60 hours to about 90 hours, about 5 minutes to about 24 hours, about 24 hours to about 48 hours, or about 5 minutes to about 48 hours.

The temperature of an environment in which a tissue, sheet, or suitable washing medium is placed may change or may not change over time. As used herein, a temperature of an environment "changes over time" when the environment (e.g., the interior of a container such as a bottle or bag) is placed in surroundings (e.g., a room, oven, refrigerator, freezer, lyophilizer, or water bath) such that the environment and its surroundings are not initially at thermal equilibrium. As used herein, a temperature of an environment "does not change over time" when the environment is at thermal equilibrium with its surroundings. Thermal equilibrium includes a temperature differential of less than about 1° C. In some embodiments, thermal equilibrium includes a temperature differential of less than about 2° C. or 3° C.

F. Exemplary Embodiments for Sterilizing or Preserving

Any tissue, sheet, or composition described herein may be sterilized before, during, or after processing, including after final packaging. Sterilizing may be performed using one or more of any number of techniques, including but not limited to exposure to gamma radiation, E-beam radiation, ethylene oxide with a stabilizing gas (such as carbon dioxide or hydrochlorofluorocarbons (HCFC)), peracetic acid, hydrogen peroxide gas plasma, or ozone.

Any tissue, sheet, or composition as described herein may be stored in a suitable preservation medium at a suitable temperature for a suitable amount of time. In one embodiment, a tissue, sheet, or composition is placed in a container containing a suitable preservation medium, such as water, a saline solution, petrolatum, petroleum jelly, Vaseline, soft paraffin, glycerol, or Ringer's solution. In another embodiment, a tissue, sheet, or composition is stored at refrigeration temperature for a limited time. In a further embodiment, a tissue, sheet, or composition is stored at refrigeration temperature in a container containing a suitable preservation medium, such as those listed above. For example, a tissue, sheet, or composition produced according to the methods described herein may be stored at a temperature of about 1° C. to about 12° C. for about 6 hours, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, or about 90 hours, less than any value listed above, greater than any value listed above, at least any value listed above, or a range of values bounded by any two of the values listed above, such as about 6 hours to about 36 hours, about 36 hours to about 60 hours, about 60 hours to about 90 hours, or about 6 hours to about 90 hours.

A tissue, sheet, or composition as described herein may also be preserved by cryopreservation, refrigeration, freezing, or dehydration. A tissue, sheet, or composition may be preserved at any processing step.

A tissue, sheet, or composition may be cryopreserved by freezing at e.g., liquid nitrogen or dry ice temperature, or a temperature of about −200° C. to about −40° C., −200° C. to about −70° C., about −200° C. to about −190° C., or −86° C. to about −78° C. and storing at liquid nitrogen temperatures for up to about 5 years. For example, a tissue, sheet, or composition may be exposed to 5% dimethylsulfoxide (DMSO) and 5% serum in DMEM and frozen slowly or rapidly.

A tissue, sheet, or composition may be stored at refrigeration temperature for a limited time. For example, a tissue, sheet, or composition may be stored at a temperature of about 1° C. to about 12° C. or about 1° C. to about 5° C. for a time of about 6 hours, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, about 90 hours, or less than any time listed above, longer than any time listed above, at least any time listed above, or a range of times bounded by any two of the times listed above, such as about 6 hours to about 36 hours, about 36 hours to about 60 hours, about 60 hours to about 90 hours, or about 6 hours to about 90 hours.

A tissue, sheet, or composition produced according to the methods described herein may be dehydrated, for example by lyophilization, by dehydration in an oven, using chemicals, or by any number of methods known in the art.

In some embodiments, a tissue, sheet, or composition may be dehydrated by lyophilization. See, e.g., U.S. Pat. No. 4,001,994 for a discussion of freeze-drying techniques. In some embodiments, a product may be frozen then lyophilized. For example, a tissue, sheet, or composition may be quickly frozen by 100% ethanol and dry ice before lyophilizing or frozen less rapidly before lyophilizing. In some embodiments, a tissue, sheet, or composition may be stored for a period of time at a freezing temperature before lyophilization, such as for about 5 minutes, about 15 minutes, about 30 minutes, about 1 hour, about 2 hours, about 3 hours, about 6 hours, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, or about 90 hours, less than any value listed above, greater than any value listed above, at least any value listed above, or a range of values bounded by any two of the values listed above, such as about 5 minutes to about 30 minutes, about 30 minutes to about 1 hour, about 1 hour to about 18 hours, about 18 hours to about 36 hours, about 36 hours to about 60 hours, about 60 hours to about 90 hours, about 5 minutes to about 24 hours, about 24 hours to about 90 hours, or about 5 minutes to about 90 hours.

A tissue, sheet, or composition may also be dehydrated by chemical dehydration, for example by using a dehydration fluid that decreases the water content of the product. A dehydration fluid may be a fluid comprising an alcohol, an organic solvent, a hydrophilic polymer (e.g., polyoxyethylene oxide), a polysaccharide (such as a cellulose derivative or dextrose, etc.), or a salt.

In some embodiments, a tissue, sheet, or composition may be stored for an extended period at a freezing, refrigeration, or room temperature. As used herein, a "freezing temperature" refers to a temperature of about 0° C. or lower (e.g., a freezing temperature may be a range of from about 0° C. to about −25° C., of from about 0° C. to about −45° C., of from about 0° C. to about −86° C., etc.). As used herein, a "refrigeration temperature" refers to a temperature of from about 1° C. to about 12° C., and a "room temperature" refers to a temperature of from about 13° C. to about 25° C. For example, a tissue, sheet or composition may be stored at a temperature of about −85° C. to about 25° C. for weeks to years depending on the storage temperature. In a further embodiment, a tissue, sheet, or composition may be stored for an extended period at liquid nitrogen temperatures, for example for a period of up to about 5 years.

G. Exemplary Embodiments for Characterizing Tissue or Sheets

The dry mass of a tissue or a sheet prepared according to the methods described herein may range from less than about one milligram per square centimeter to greater than about 25 milligrams per square centimeter. The dry mass per surface area ($mg/cm^2$) of a tissue or sheet may be calculated by dividing the mass of the tissue or sheet by its surface area. For example, a tissue or a sheet may have a dry mass of about 1 $mg/cm^2$, about 2 $mg/cm^2$, about 3 $mg/cm^2$, about 4 $mg/cm^2$, about 5 $mg/cm^2$, about 6 $mg/cm^2$, about 7 $mg/cm^2$, about 8 $mg/cm^2$, about 9 $mg/cm^2$, about 10 $mg/cm^2$, about 11 $mg/cm^2$, about 12 $mg/cm^2$, about 13 $mg/cm^2$, about 14 $mg/cm^2$, about 15 $mg/cm^2$, about 16 $mg/cm^2$, about 17 $mg/cm^2$, about 18 $mg/cm^2$, about 19 $mg/cm^2$, about 20 $mg/cm^2$, about 21 $mg/cm^2$, about 22 $mg/cm^2$, about 23 $mg/cm^2$, about 24 $mg/cm^2$, or about 25 $mg/cm^2$, or less than any value listed above, greater than any value listed above, at least any value listed above, or a range of values bounded by any two of the values listed above, such as about 1 $mg/cm^2$ to about 25 $mg/cm^2$, about 1 $mg/cm^2$ to about 12 $mg/cm^2$, about 12 $mg/cm^2$ to about 25 $mg/cm^2$, about 1 $mg/cm^2$ to about 5 $mg/cm^2$, about 5 $mg/cm^2$ to about 10 $mg/cm^2$, about 10 $mg/cm^2$ to about 15 $mg/cm^2$, about 15 $mg/cm^2$ to about 20 $mg/cm^2$, about 20 $mg/cm^2$ to about 25 $mg/cm^2$.

The water absorption potential of a tissue or a sheet prepared according to the methods described herein may range from less than about one milligram per square centimeter to greater than about 40 milligrams per square centimeter. The water absorption potential of a tissue or a sheet (e.g., a dehydrated tissue or a dehydrated sheet) may be determined by subtracting the mass of the tissue or sheet before hydrating from its mass after hydrating and dividing by the surface area of the tissue or sheet. For example, a tissue or a sheet may have a water absorption potential of about 1 $mg/cm^2$, about 2 $mg/cm^2$, about 3 $mg/cm^2$, about 4 $mg/cm^2$, about 5 $mg/cm^2$, about 6 $mg/cm^2$, about 7 $mg/cm^2$, about 8 $mg/cm^2$, about 9 $mg/cm^2$, about 10 $mg/cm^2$, about 11 $mg/cm^2$, about 12 $mg/cm^2$, about 13 $mg/cm^2$, about 14 $mg/cm^2$, about 15 $mg/cm^2$, about 16 $mg/cm^2$, about 17 $mg/cm^2$, about 18 $mg/cm^2$, about 19 $mg/cm^2$, about 20 $mg/cm^2$, about 21 $mg/cm^2$, about 22 $mg/cm^2$, about 23 $mg/cm^2$, about 24 $mg/cm^2$, about 25 $mg/cm^2$, about 26 $mg/cm^2$, about 27 $mg/cm^2$, about 28 $mg/cm^2$, about 29 $mg/cm^2$, about 30 $mg/cm^2$, about 31 $mg/cm^2$, about 32 $mg/cm^2$, about 33 $mg/cm^2$, about 34 $mg/cm^2$, about 35 $mg/cm^2$, about 36 $mg/cm^2$, about 37 $mg/cm^2$, about 38 $mg/cm^2$, about 39 $mg/cm^2$, or about 40 $mg/cm^2$, or less than any value listed above, greater than any value listed above, at least any value listed above, or a range of values bounded by any two of the values listed above, such as about 1 $mg/cm^2$ to about 40 $mg/cm^2$, about 1 to about 20 $mg/cm^2$, about 20 to about 40 $mg/cm^2$, about 1 $mg/cm^2$ to about 5 $mg/cm^2$, about 5 $mg/cm^2$, to about 10 $mg/cm^2$, about 10 $mg/cm^2$ to about 15 $mg/cm^2$, about 15 $mg/cm^2$ to about 20 $mg/cm^2$, about 20 $mg/cm^2$ to about 30 $mg/cm^2$, about 30 $mg/cm^2$ to about 40 $mg/cm^2$.

Total protein content of a tissue or a sheet prepared according to the methods described herein may range from less than about 25 microgram per square centimeter to greater than about 2 milligrams per square centimeter. For example, a tissue or a sheet may have a total protein content of about 25 $\mu g/cm^2$, about 50 $\mu g/cm^2$, about 75 $\mu g/cm^2$, about 100 $\mu g/cm^2$, about 125 $\mu g/cm^2$, about 150 $\mu g/cm^2$, about 175 $\mu g/cm^2$, about 200 $\mu g/cm^2$, about 225 $\mu g/cm^2$, about 250 $\mu g/cm^2$, about 275 $\mu g/cm^2$, about 300 $\mu g/cm^2$, about 325 $\mu g/cm^2$, about 350 $\mu g/cm^2$, about 375 $\mu g/cm^2$, about 400 $\mu g/cm^2$, about 425 $\mu g/cm^2$, about 450 $\mu g/cm^2$, about 475 $\mu g/cm^2$, about 500 $\mu g/cm^2$, about 525 $\mu g/cm^2$, about 550 $\mu g/cm^2$, about 575 $\mu g/cm^2$, about 600 $\mu g/cm^2$, about 625 $\mu g/cm^2$, about 650 $\mu g/cm^2$, about 675 $\mu g/cm^2$, about 700 $\mu g/cm^2$, about 725 $\mu g/cm^2$, about 750 $\mu g/cm^2$, about 775 $\mu g/cm^2$, about 800 $\mu g/cm^2$, about 825 $\mu g/cm^2$, about 850 $\mu g/cm^2$, about 875 $\mu g/cm^2$, about 900 $\mu g/cm^2$, about 925 $\mu g/cm^2$, about 950 $\mu g/cm^2$, about 975 $\mu g/cm^2$, about 1000 $\mu g/cm^2$, about 1025 $\mu g/cm^2$, about 1050 $\mu g/cm^2$, about 1075 $\mu g/cm^2$, about 1100 $\mu g/cm^2$, about 1125 $\mu g/cm^2$, about 1150 $\mu g/cm^2$, about 1175 $\mu g/cm^2$, about 1200 $\mu g/cm^2$, about 1225 $\mu g/cm^2$, about 1250 $\mu g/cm^2$, about 1275 $\mu g/cm^2$, about 1300 $\mu g/cm^2$, about 1325 $\mu g/cm^2$, about 1350 $\mu g/cm^2$, about 1375 $\mu g/cm^2$, about 1400 $\mu g/cm^2$, about 1425 $\mu g/cm^2$, about 1450 $\mu g/cm^2$, about 1475 $\mu g/cm^2$, about 1500 $\mu g/cm^2$, about 1525 $\mu g/cm^2$, about 1550 $\mu g/cm^2$, about 1575 $\mu g/cm^2$, about 1600 $\mu g/cm^2$, about 1625 $\mu g/cm^2$, about 1650 $\mu g/cm^2$, about 1675 $\mu g/cm^2$, about 1700 $\mu g/cm^2$, about 1725 $\mu g/cm^2$, about 1750 $\mu g/cm^2$, about 1775 $\mu g/cm^2$, about 1800 $\mu g/cm^2$, about 1825 $\mu g/cm^2$, about 1850 $\mu g/cm^2$, about 1875 $\mu g/cm^2$, about 1900 $\mu g/cm^2$, about 1925 $\mu g/cm^2$, about 1950 $\mu g/cm^2$, about 1975 $\mu g/cm^2$, or about 2000 $\mu g/cm^2$, or less than any value listed above, greater than any value listed above, at least any value listed above, or a range of values bounded by any two of the values listed above, such as about 25 $\mu g/cm^2$ to about 100 $\mu g/cm^2$, about 100 $\mu g/cm^2$ to about 500 $\mu g/cm^2$, about 500 $\mu g/cm^2$ to about 1000 $\mu g/cm^2$, about 1000 $\mu g/cm^2$ to about 1500 $\mu g/cm^2$, about 1500 $\mu g/cm^2$ to about 2000 $\mu g/cm^2$, about 25 $\mu g/cm^2$ to about 500 $\mu g/cm^2$, about 500 $\mu g/cm^2$ to about 1500 $\mu g/cm^2$, about 1000 $\mu g/cm^2$ to about 2000 $\mu g/cm^2$, or about 25 $\mu g/cm^2$ to about 2000 $\mu g/cm^2$.

A tissue or a sheet may have a total protein content of about 0.1 $mg/cm^2$, about 0.2 $mg/cm^2$, about 0.3 $mg/cm^2$, about 0.4 $mg/cm^2$, about 0.5 $mg/cm^2$, about 0.6 $mg/cm^2$, about 0.7 $mg/cm^2$, about 0.8 $mg/cm^2$, about 0.9 $mg/cm^2$, about 1.0 $mg/cm^2$, about 1.1 $mg/cm^2$, about 1.2 $mg/cm^2$, about 1.3 $mg/cm^2$, about 1.4 $mg/cm^2$, about 1.5 $mg/cm^2$, about 1.6 $mg/cm^2$, about 1.7 $mg/cm^2$, about 1.8 $mg/cm^2$, about 1.9 $mg/cm^2$, or about 2.0 $mg/cm^2$, or less than any value listed above, greater than any value listed above, at least any value listed above, or a range of values bounded by any two of the values listed above, such as about 0.1 $mg/cm^2$ to about 1 $mg/cm^2$, about 1 $mg/cm^2$ to about 1.5 $mg/cm^2$, about 1.5 $mg/cm^2$ to about 2 $mg/cm^2$, or about 0.1 $mg/cm^2$ to about 2 $mg/cm^2$. A procedure for determining total protein content is provided in Example 17 below.

Hemoglobin is a major component of erythrocytes (or red blood cells) and is responsible for the cells' characteristic red color. The hemoglobin content of a tissue or a sheet prepared according to the methods described herein may range from less than about 13 nanograms per milligram of dry mass of the tissue or sheet to about 0.01 nanogram per milligram of dry mass of the tissue or sheet. The hemoglobin content of a tissue or a sheet is the ratio of hemoglobin mass to mass of the tissue or sheet. For example, a tissue or a sheet may have a hemoglobin content of about 13 ng/mg, about 12 ng/mg, about 11 ng/mg, about 10 ng/mg, about 9 ng/mg, about 8 ng/mg, about 7 ng/mg, about 6 ng/mg, about 5 ng/mg, about 4 ng/mg, about 3 ng/mg, about 2 ng/mg, about 1 ng/mg, about 0.9 ng/mg, about 0.8 ng/mg, about 0.7 ng/mg, about 0.6 ng/mg, about 0.5 ng/mg, about 0.4 $\mu g/mg$, about 0.3 ng/mg, about 0.2 ng/mg, about 0.1 ng/mg, about 0.09 ng/mg, about 0.08 ng/mg, about 0.07 ng/mg, about 0.06 ng/mg, about 0.05 ng/mg, about 0.04 ng/mg, about 0.03 ng/mg, about 0.02 ng/mg, or about 0.01 ng/mg, or less than any value listed above, greater than any value listed above, at least any value listed above, or a range of values bounded by any two of the values listed above, such as about 0.01 ng/mg to about 0.05 ng/mg, about 0.05 ng/mg to about 0.1 ng/mg, about 0.1 ng/mg to about 0.5 ng/mg, about 0.5 ng/mg to about 1 ng/mg, about 1 ng/mg to about 5 ng/mg, about 5 ng/mg to about 10 ng/mg, about 10 ng/mg to about 13 ng/mg, about 0.01 ng/mg to about 13 ng/mg, about 0.01 ng/mg to about 0.1 ng/mg, about 0.1 ng/mg to about 1 ng/mg, about 1 ng/mg to about 10 ng/mg, or about 1 ng/mg to about 13 ng/mg. A procedure for determining hemoglobin content is provided in Example 18 below.

Thickness of placental tissue and the thickness of layers within the tissue can vary from donor to donor and can vary across the same placental tissue obtained from the same donor. In addition, thickness of placental tissue and its layers may be greater in some species than others. Mean thickness of a tissue or a sheet prepared according to the methods described herein may range from less than about 10 micrometers to greater than about 2 millimeters. Mean thickness of the intermediate layer of a tissue or sheet prepared according to the methods described herein may range from less than about one micrometer to greater than about 600 micrometers. Mean thickness may be determined by measuring the approximate thickness of the tissue or sheet or the approximate thickness of the intermediate layer at two or more representative areas. A procedure for determining mean thickness is provided in Example 19 below.

For example, a tissue or sheet may have a mean thickness of about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm, about 390 µm, about 400 µm, about 410 µm, about 420 µm, about 430 µm, about 440 µm, about 450 µm, about 460 µm, about 470 µm, about 480 µm, about 490 µm, about 500 µm, about 510 µm, about 520 µm, about 530 µm, about 540 µm, about 550 µm, about 560 µm, about 570 µm, about 580 µm, about 590 µm, about 600 µm, about 700 µm, about 710 µm, about 720 µm, about 730 µm, about 740 µm, about 750 µm, about 760 µm, about 770 µm, about 780 µm, about 790 µm, about 800 µm, about 810 µm, about 820 µm, about 830 µm, about 840 µm, about 850 µm, about 860 µm, about 870 µm, about 880 µm, about 890 µm, about 900 µm, about 910 µm, about 920 µm, about 930 µm, about 940 µm, about 950 µm, about 960 µm, about 970 µm, about 980 µm, about 990 µm, about 1000 µm (about 1 mm), about 1100 µm, about 1200 µm, about 1300 µm, about 1400 µm, about 1500 µm, about 1600 µm, about 1700 µm, about 1800 µm, about 1900 µm, about 2000 µm (about 2 mm), or less than any value listed above, greater than any value listed above, at least any value listed above, or a range of values bounded by any two of the values listed above, such as about 10 µm to about 50 µm, about 50 µm to about 100 µm, about 10 µm to about 100 µm, about 100 µm to about 250 µm, about 10 µm to about 250 µm, about 10 µm to about 500 µm, about 250 µm to about 500 µm, about 500 µm to about 750 µm, about 750 µm to about 1 mm, about 1 mm to about 2 mm, about 1000 µm to about 1500 µm, about 10 µm to about 2 mm, about 10 µm to about 1 mm, or about 10 µm to about 2 mm. In addition, a composition may comprise a tissue or a sheet having a mean thickness of any value or range of values listed above.

In addition, the intermediate layer of a tissue or sheet may have a mean thickness of about 1 µm, about 2 µm, about 3 µm, about 4 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 80 µm, about 90 µm, about 100 µm, about 110 µm, about 120 µm, about, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm, about 390 µm, about 400 µm, about 410 µm, about 420 µm, about 430 µm, about 440 µm, about 450 µm, about 460 µm, about 470 µm, about 480 µm, about 490 µm, about 500 µm, about 510 µm, about 520 µm, about 530 µm, about 540 µm, about 550 µm, about 560 µm, about 570 µm, about 580 µm, about 590 µm, or about 600 or less than any value listed above, greater than any value listed above, at least any value listed above, or a range of values bounded by any two of the values listed above, such as about 1 µm to about 5 µm, about 5 µm to about 25 µm, about 25 µm to about 50 µm, about 50 µm to about 100 µm, about 100 µm to about 250 µm, about 250 µm to about 500 µm, about 100 µm to about 600 µm, about 1 µm to about 600 µm, about 1 µm to about 100 µm, about 10 µm to about 100 µm, or about 50 µm to about 500 µm. Furthermore, a composition may comprise a tissue or a sheet with an intermediate layer having a mean thickness of any value or range of values listed above.

The presence of nucleated cells, extracellular matrix molecules, growth factors, and other biomolecules in a tissue or sheet prepared according to the methods described herein may be determined. ELISA kits and staining procedures for identifying some components are provided in Example 20. In some embodiments, a tissue or sheet comprises bFGF, EGF, TGF beta 1, PDGF-AA, PDGF-BB, TIMP-1, TIMP-2, TIMP-4, or hyaluronic acid. In some embodiments, a tissue or sheet comprises nucleated cells and extracellular matrix molecules such as collagens, glycosaminoglycan-containing molecules (e.g., proteoglycans, etc.), or elastins.

H. Exemplary Embodiments for Layering Sheets

In some embodiments, another sheet may be layered on a surface of a perforated, unseparated amnion/chorion; a perforated, separated amnion, or a perforated, separated chorion before or after preservation using methods understood by those of ordinary skill in the art. For example, one or more perforated or unperforated, unseparated amnion/chorion may be layered on a perforated, unseparated amnion/chorion; a perforated, separated amnion; or a perforated, separated chorion. In other embodiments, one or more perforated or unperforated separated amnion may be layered on a perforated, unseparated amnion/chorion; a perforated, separated amnion; or a perforated, separated chorion. In further embodiments, one or more perforated or unperforated separated chorion may be layered on a perforated, unseparated amnion/chorion; a perforated, separated amnion; or a perforated, separated chorion. Moreover, perforated and unperforated separated amnion and chorion sheets can be layered on a perforated, unseparated amnion/chorion sheet in any number, combination, order, direction, or orientation.

I. Exemplary Embodiments for Powderizing

A tissue, sheet, or composition prepared according to the methods described herein may also be powderized. As used herein, "powderizing" refers to milling, mincing, grinding, pulverizing, or any combination thereof to produce a powder.

In some embodiments, a tissue, sheet, or composition is milled, minced, ground, pulverized, or any combination thereof into a powder product by any method known in the art. For example, a cryopreserved tissue, sheet, or composition may be powderized using a cryogenic impact grinder (e.g., the 6770, 6870, 6970D, or 6970EFM Spex Freezer/Mill® (Metuchen, N.J.)).

J. Exemplary Embodiments for Marking

A tissue, sheet, or composition prepared according to the methods described herein may be transparent or whitish in color, and it may be difficult to discern orientation of the tissue, sheet, or composition. In some embodiments, the tissue, sheet, or composition may have a marking, such as an embossment, a stain, a tint, a stamp, or a cut. The stain, tint, or stamp may be of any hue, including any shade of pink, red, blue, violet, orange, yellow, or green. Such a marking may be used to orient the user to as to the direction or orientation of the tissue, sheet, or composition. In some embodiments, the marking is made using one or more dyes (e.g., a natural dye, a vegetable dye, a hypoallergenic dye, beet juice, etc.). The dye may be of any hue, including any shade of pink, red, blue, violet, orange, yellow, or green. Any one or more layers of the tissue, sheet, or composition may be dyed, including, but not limited to, the epithelial layer of the amnion, the basement membrane of the amnion, the compact layer of the amnion, and the fibroblast layer of the amnion, the intermediate layer, the reticular layer of the chorion, the basement membrane of the chorion, and the trophoblast layer of the chorion. The dye may be applied to the tissue, sheet, or composition using any number of methods, including stamped on, painted on, or diffused into the tissue, sheet, or composition.

K. Exemplary Embodiments for Wound Healing

The compositions and products described herein may be used in wound healing and applied to the eye, the skin, a nerve, a tendon, or the dura of a subject in need of treatment. For example, the compositions and products may be applied to a wound of the eye, such as a burn, a laceration, a corneal ulceration, a conjunctival lesion, or a surgical wound. The compositions and products may be applied to a wound of the skin, for example, a burn, a laceration, a diabetic ulcer, a venous ulcer, an arterial ulcer, a decubitus ulcer, or a surgical wound. Techniques for applying the compositions and products to a wound of the eye, skin, nerve, tendon, or dura are understood by those of ordinary skill in the art.

EXAMPLES

Example 1

Preparing Perforated, Unseparated Amnion/Chorion Sheets

A placenta collected from a donor mother is placed in sealed bag containing a suitable storage medium and is shipped on wet ice to the laboratory. After receipt, the placenta is stored at refrigeration temperature. The placenta is removed from its bag for processing at room temperature. The placenta is transferred to a metal tray. Using a pair of surgical scissors, the unseparated amnion/chorion is dissected from the placental disc and umbilical cord. The unseparated amnion/chorion sheet is transferred to a 1 L Nalgene® plastic screw-top bottle containing about 750 mL of a sodium chloride solution and placed on a rocker platform and gently agitated for approximately 1 hour at room temperature.

The unseparated amnion/chorion is transferred to a cutting mat and cut into multiple sheets using a rotary blade. An unseparated amnion/chorion sheet is placed on a rubber or silicon mat (or other soft, nonporous surface that will allow a perforator to penetrate the tissue) with the epithelial layer of the amnion facing up. The unseparated amnion/chorion sheet is perforated, for example, by rolling a perforator device (e.g., a device having a wooden handle and steel roller with a series pins arranged in multiple rows) across the top surface of the sheet such that multiple series of holes are made that traverse the thickness of the amnion/chorion sheet.

The sheet is transferred to another 1 L bottle containing about 750 mL of a sodium chloride solution and placed on the rocker and gently agitated for about 1 hour at room temperature. The sheet is then transferred to a 1 L bottle containing about 750 mL of sterile water or a sodium chloride solution and placed on the rocker at room temperature with gentle agitation for about 1.5 hours followed by no agitation for another about 1.5 hours without changing the solution.

The sheet is then transferred to a 1 L bottle containing about 750 mL of sterile water or a sodium chloride solution and stored at refrigeration temperature for a period of up to several days before lyophilization. After storage and before lyophilization, the sheet is transferred to a 1 L bottle containing about 750 mL of sterile water or a sodium chloride solution and placed on the rocker at room temperature with gentle agitation for about 1.5 hours followed by no agitation for an additional about 1.5 hours without changing the solution. The sheet is then stored in sterile water at a freezing temperature overnight and then lyophilized until dry.

Example 2

Preparing Perforated, Unseparated Amnion/Chorion Layered With a Separated Sheet

Following collection of a placenta, dissection of the unseparated amnion/chorion away from the placental disc, and washing in a sodium chloride solution, the unseparated amnion/chorion is cut into multiple sheets using a rotary blade as described in Example 1. Two sheets are placed on a mat with the epithelial layer of the amnion facing down. The chorion is gently separated from the amnion of each sheet by hand and placed on the mat. One of the separated amnion sheets and one of the separated chorion sheets is perforated, for example, by rolling a perforator device across the sheets such that several holes are made that traverse the thickness of the sheets. The other separated amnion sheet and the other separated chorion sheet are not perforated.

The perforated and unperforated separated amnion sheets and chorion sheets are transferred to a 1 L bottle containing about 750 mL of a suitable washing medium (e.g., sterile water or a sodium chloride solution), placed on a rocker, and gently agitated for about 1 hour at room temperature. The suitable washing medium is replaced with about 750 mL of the same or a different suitable washing medium and gently agitated at room temperature for about 1.5 hours followed by no agitation for another about 1.5 hours without changing the solution. The sheets are then transferred to a 1 L bottle containing about 750 mL of a suitable washing medium and stored at refrigeration temperature for a period of up to several days.

Four perforated, unseparated amnion/chorion sheets are prepared according to the method of Example 1 through the step of storing at refrigeration temperature and before lyophilization. After transferring the perforated, unseparated amnion/chorion sheets; the perforated, separated amnion sheet; the perforated, separated chorion sheet; the unperforated, separated amnion sheet; and the unperforated, separated chorion sheet to about 750 mL of a suitable washing medium, the sheets are gently agitated at room temperature for about 1.5 hours followed by no agitation for an additional about 1.5 hours without changing the solution.

The four perforated, unseparated amnion/chorion sheets are each placed on a solid surface with either the epithelial layer of the amnion facing upward or downward. A separated sheet is layered on top of one of the perforated, unseparated amnion/chorion sheets such that either side of the separated sheet is facing up. After storing the layered sheets at a freezing temperature overnight, they are lyophilized until dry.

Example 3

Preparing Partial Perforations of Unseparated Amnion/Chorion

Following collection of a placenta, dissection of the unseparated amnion/chorion away from the placental disc, and washing in a suitable washing medium, the unseparated amnion/chorion is cut into two sheets using a rotary blade as described in Example 1. The sheets are then placed on a mat with the epithelial layer of one sheet facing up and the epithelial layer of the other sheet facing down.

A perforating roller device having pins of varying length is rolled across the surface of the sheets to create perforations of varied depth. For example, a roller having pins with a length ranging from 0.1 µm or less to 1 mm or greater may be used to create partial perforations.

Example 4

Process A

Donor placentas were logged and quarantined in the freezer until results from serological testing were received indicating that the placentas were nonreactive. Each placenta was processed separately according to the following procedure. The bag containing the donor placenta was placed on a tray. The placenta was transferred from the bag to another tray by grasping the umbilical cord. The unseparated amnion/chorion was then carefully dissected away from the placental disc. The umbilical cord and placental disc were then discarded. Using fingertips, some visible, removable blood clots were gently lifted away from the outer surfaces of the unseparated amnion/chorion to reduce the amount of blood entering the first washing medium.

A portion of the unseparated amnion/chorion tissue was placed in a 1 L Nalgene® screw-top bottle to which about 750 mL of a first suitable washing medium was added. For Process A, the first washing medium used was 26% sodium chloride maintained at room temperature. The bottle was closed and gently agitated for 1 hour at room temperature. In this example and the following examples, gentle agitation was achieved by using a rocker at about 30 RPM.

The unseparated amnion/chorion was then removed and laid flat on a soft, nonporous mat with the epithelial layer of the amnion facing up. The first washing medium was discarded. Using fingertips, additional visible, removable blood clots were gently lifted away from the tissue's outer surfaces. Blood-tinted areas of the unseparated amnion/chorion tissue were gently massaged using fingertips with care so as not to separate the tissue.

To perforate the unseparated amnion/chorion, a perforating roller was placed on top of the center of the tissue and rolled outwards over the surface of the tissue. The perforating roller used had a metal roller head with 24×7 rows of metal pins spaced about 6 mm apart.

Next, the perforated, unseparated amnion/chorion was placed back into the empty bottle to which about 750 mL of a second suitable washing medium was added. For Process A, the second washing medium used was purified water maintained at room temperature. The bottle was closed and gently agitated for 1.5 hours at room temperature.

The second washing medium was decanted and replaced with about 750 mL of a third suitable washing medium. For Process A, the third washing medium used was 26% sodium chloride maintained at room temperature. After closing the bottle, it was gently agitated for 1 hour at room temperature.

After removing the third washing medium, about 750 mL of a fourth suitable washing medium was added. For Process A, the fourth washing medium used was 26% sodium chloride maintained at room temperature. The sample was then refrigerated (at about 4° C.) overnight.

The next morning, the fourth washing medium was decanted and replaced with about 750 mL of a fifth suitable washing medium. For Process A, the fifth washing medium used was purified water maintained at room temperature. After closing the bottle, it was gently agitated for 1 hour at room temperature.

The tissue was removed and placed in a closed container and stored overnight at a freezing temperature (about −20° C.). The frozen tissue was then lyophilized overnight at about −46° C. The lyophilized tissue was placed into a container, labeled, and sealed.

Example 5

Process B

The steps of Process A were performed with the exception that (1) the perforating step was performed after the placental disc and umbilical cord were removed and prior to the step involving the first washing medium; (2) the first washing medium used was purified water instead of 26% sodium chloride; (3) the second washing medium used was 26% sodium chloride instead of purified water; and (4) the overnight refrigeration step involving the third washing medium and the gentle agitation step involving the fourth washing medium were performed in reverse order.

Example 6

Process C

The steps of Process A were performed with the exception that prior to the addition of each of the first, second, third, fourth, and fifth washing medium, the mediums were preheated in a water bath maintained at 37° C.

Example 7

Process D

The steps of Process A were performed with the exception that the overnight refrigeration step involving the third washing medium and the gentle agitation step involving the fourth washing medium were performed in reverse order.

Example 8

Process E

The steps of Process A were performed with the exception that (1) the overnight refrigeration step involving the third washing medium and the gentle agitation step involving the fourth washing medium were performed in reverse order, and (2) prior to the addition of each of the first, second, and fourth washing mediums (the washing steps performed during the first day for Process E), the mediums were preheated in a waterbath maintained at 37° C.

Example 9

Process F

The steps of Process A were performed with the exception that (1) the overnight refrigeration step involving the third washing medium and the gentle agitation step involving the fourth washing medium were performed in reverse order, and (2) prior to the addition of each of the first, second, third, fourth, and fifth washing mediums, the mediums were preheated in a waterbath maintained at 37° C.

Example 10

Process G

The steps of Process A were performed with the exception that the step involving a third washing medium was not performed.

Example 11

Process H

The steps of Process A were performed with the exception that (1) the step involving a third washing medium was not performed, and (2) prior to the addition of each of the first, second, fourth, and fifth washing mediums, the mediums were preheated in a waterbath maintained at 37° C.

Example 12

Process I

The steps of Process A were performed with the exception that (1) the step involving a third washing medium was not performed, and (2) for the step involving the first washing medium, the bottle containing the tissue was gently agitated for 2 hours at room temperature.

Example 13

Processes $J_a$-$J_i$

The steps of Processes A-I were performed with the exception that the unseparated amnion/chorion tissue was not perforated. "Process $J_a$" refers to the process in which the steps were as in Process A except that the unseparated amnion/chorion tissue was not perforated; "Process $J_b$" refers to the process in which the steps were as in Process B except that the unseparated amnion/chorion tissue was not perforated; and so on.

Example 14

Processes $K_a$-$K_i$ and $K_{Ja}$-$K_{Ji}$

The steps of Processes A-I and $J_a$-$J_i$ were performed with the exception that instead of freezing the tissue overnight followed by lyophilizing the tissue overnight, the sample was oven dried overnight at about 35° C. "Process $K_a$" refers to the process in which the steps were as in Process A except that instead of freezing the tissue overnight followed by lyophilizing the tissue overnight, the sample was oven dried overnight at about 35° C.; "Process $K_b$" refers to the process in which the steps were as in Process B except that instead of freezing the tissue overnight followed by lyophilizing the tissue overnight, the sample was oven dried overnight at about 35° C.; and so on. "Process $K_{Ja}$" refers to the process in which the steps were as in process $J_a$ except that instead of freezing the tissue overnight followed by lyophilizing the tissue overnight, the sample was oven-dried overnight at about 35° C.; "Process $K_{Jb}$" refers to the process in which the steps were as in Process $J_b$ except that instead of freezing the tissue overnight followed by lyophilizing the tissue overnight, the sample was oven dried overnight at about 35° C.; and so on.

Example 15

Dry Mass

The dry mass per surface area (mg/cm$^2$) of processed, unseparated amnion/chorion tissue was measured and compared to that of unprocessed, unseparated amnion/chorion tissue. The results are summarized in Table 1.

TABLE 1

| Unseparated amnion/chorion tissue | n | n includes Processes | Dry Mas per Surface Area (mg/cm$^2$) | |
|---|---|---|---|---|
| | | | Mean | Range |
| Unprocessed, lyophilized | 9 | n/a | 11.7 | 5.6-20.3 |
| Unprocessed, oven-dried | 3 | n/a | 8.9 | 6.6-14.0 |
| Processed, perforated, lyophilized | 15 | A, B, C, D, E, F, H | 9.8 | 4.9-16.0 |
| Processed, unperforated, lyophilized | 9 | $J_c$, $J_d$, $J_f$ | 7.3 | 5.4-9.4 |
| Processed, perforated, oven-dried | 16 | $K_c$, $K_d$, $K_e$, $K_f$ | 7.6 | 4.5-13.8 |
| Processed, unperforated, oven-dried | 8 | $K_J$, $K_{Jd}$, $K_{Jf}$ | 6.3 | 3.4-11.3 |

Example 16

Water Absorption

The water absorption potential (mg of water absorbed per cm$^2$ of tissue) of processed, unseparated amnion/chorion tissue was compared to fresh, unprocessed, unseparated amnion/chorion tissue. A 3 cm×3 cm sheet of each sample was weighed before and after rehydration. Rehydration was achieved by placing the sample in a dish and adding 100 mL distilled water over the tissue. After 80 seconds of remaining in the distilled water, the tissue was removed, laid out on a mat, and the excess surface water wicked away using a wipe. The water absorption potential was calculated by subtracting the mass of the dried sample from the mass of the rehydrated sample and dividing by the surface area of the tissue. The water absorption potential of 3 samples of fresh, unprocessed, unseparated amnion/chorion tissue was undetectable (LOD=0.1 mg), presumably because the tissue was already fully hydrated. The results of the processed samples are summarized in Table 2.

TABLE 2

| Processed, unseparated amnion/chorion tissue | n | n includes Processes | Water absorption potential (mg absorbed/cm$^2$) Mean | Range |
|---|---|---|---|---|
| Perforated, lyophilized | 12 | C, D, F, G | 23 | 14-34 |
| Unperforated, lyophilized | 5 | $J_c$, $J_d$, $J_g$ | 17 | 11-22 |
| Perforated, oven-dried | 12 | $K_c$, $K_d$, $K_e$, $K_f$ | 10 | 3-15 |
| Unperforated, oven-dried | 6 | $K_{Jc}$, $K_{Jd}$, $K_{Je}$ | 11 | 9-13 |

Example 17

Protein Content

Total protein content was determined for samples of processed, unseparated amnion/chorion tissue and for fresh, unprocessed, unseparated amnion/chorion tissue. Total protein was extracted from the tissue samples, quantified using a Pierce™ BCA Protein Assay Kit (Thermo Scientific™, Product No. 23227), and normalized to the surface area of the sample. The results are summarized in Table 3.

TABLE 3

| Unseparated amnion/chorion tissue | n | n includes Processes | Total Protein (µg/cm$^2$) Mean | Range |
|---|---|---|---|---|
| Fresh, unprocessed | 3 | n/a | 1057 | 749-1571 |
| Processed, perforated, lyophilized | 18 | A, C, D, F, G, H | 432 | 392-597 |
| Processed, unperforated, lyophilized | 18 | $J_a$, $J_c$, $J_d$, $J_f$, $J_g$, $J_h$ | 507 | 275-844 |
| Processed, perforated, oven-dried | 10 | $K_a$, $K_c$, $K_d$, $K_f$, $K_g$, $K_h$ | 338 | 131-500 |
| Processed, unperforated, oven-dried | 8 | $K_{Ja}$, $K_{Jc}$, $K_{Jd}$, $K_{Jf}$, $K_{Jg}$, $K_{Jh}$ | 336 | 116-686 |

Example 18

Hemoglobin

The hemoglobin content of unprocessed, unseparated amnion/chorion tissue was compared to that of processed, unseparated amnion/chorion tissue that were either perforated or unperforated. Hemoglobin content was determined using a RayBio® Human Hemoglobin ELISA kit (RayBiotech, Product No. ELH-Hgb1) and normalized to the dry mass of the sample. The mean and ranges of hemoglobin content (based on the ratio of hemoglobin mass to tissue mass) are summarized in Table 4.

The limit of detection (LOD) for the hemoglobin assay as performed was considered to be 0.043 ng/mg, based on lysis of the sample in 1 mL lysis buffer per 35 mg sample and the lowest detectable hemoglobin concentration for the RayBio® Human Hemoglobin ELISA kit being 1.5 ng/mg.

TABLE 4

| Unseparated amnion/chorion tissue | n | n includes Processes | µg/mg Mean | Range |
|---|---|---|---|---|
| Unprocessed, lyophilized | 8 | n/a | 14.9 | 14.1-17.9 |
| Processed, perforated, lyophilized | 7 | A, C, F, G, H | 1.0 | 0.1-2.9 |
| Processed, unperforated, lyophilized | 7 | $J_a$, $J_c$, $J_f$, $J_g$, $J_h$ | 2.8 | <LOD-12.6 |

(LOD: limit of detection.)

Both (i) the difference in hemoglobin content between unprocessed and processed, perforated, unseparated amnion/chorion tissue and (ii) the difference in hemoglobin content between unprocessed and processed, unperforated, unseparated amnion/chorion tissue were statistically significant (p-values<0.01). The significant reduction in hemoglobin content observed in processed, unseparated amnion/chorion tissue compared to unprocessed tissue indicates a significant reduction in red blood cell remnants.

Example 19

Thickness

The thickness of processed, unseparated amnion/chorion tissue was compared to that of fresh, unprocessed, unseparated amnion/chorion tissue. The thickness of the intermediate layer of the tissues were also compared. A portion of each tissue was embedded, sectioned, mounted, and stained with hematoxylin and eosin (H & E). A digital image of each slide was obtained. Approximate thickness of the tissues and approximate thickness of the intermediate layer of the tissues were measured at five or six representative areas under ×20 magnification. Mean thicknesses of each tissue were determined by calculating the average of the measured values. The mean and range of mean thicknesses were determined for each group of samples and are summarized in Table 5.

TABLE 5

| Unseparated amnion/chorion tissue | n | n includes Processes | Thickness (µm) Mean | Range | Intermediate Layer Thickness (µm) Mean | Range |
|---|---|---|---|---|---|---|
| Fresh, unprocessed | 3 | n/a | 604 | 511-757 | 310 | 283-326 |
| Processed, perforated, lyophilized | 7 | A, F, G, H | 339 | 210-440 | 104 | 45-196 |
| Processed, unperforated, lyophilized | 5 | $J_a$, $J_g$, $J_h$ | 472 | 262-679 | 66 | 54-86 |
| Processed, perforated, oven-dried | 3 | $K_f$, $K_i$ | 158 | 122-220 | 42 | 22-65 |
| Processed, unperforated, oven-dried | 3 | $K_{Jf}$, $K_{Ji}$ | 243 | 101-432 | 55 | 26-75 |

Example 20

Growth Factors, Extracellular Matrix Molecules, and Other Biomolecules

The presence of various growth factors and other biomolecules in processed, unseparated amnion/chorion tissues was determined using ELISA kits that assay for bFGF, EGF, TGF beta 1, PDGF-AA, PDGF-BB, TIMP-1, TIMP-2, and TIMP-4 (RayBiotech, RayBio® ELISA kits Product Nos. ELH-bFGH, ELH-EGF, ELH-TGFb1, ELH-PDGFAA, ELH-PDGFBB, ELH-TIMP1, ELH-TIMP2, and ELH-TIMP4), and for hyaluronic acid (R&D Systems, Hyaluronan Quantikine ELISA Product No. DHYAL0). Samples of processed, unseparated amnion/chorion tissue were found to contain bFGF, EGF, TGF beta 1, PDGF-AA, PDGF-BB, TIMP-1, TIMP-2, TIMP-4, and hyaluronic acid regardless of whether they were perforated or unperforated, and of whether they were lyophilized or oven-dried.

The presence of nucleated cells and extracellular matrix molecules in processed, unseparated amnion/chorion tissue was determined by standard histological staining Unseparated amnion/chorion tissue was prepared according to Process $K_i$ and $K_{ji}$. A portion of each tissue was embedded, sectioned, mounted, and stained. The presence of nucleated cells (H & E), collagens (Masson's Trichrome), glycosaminoglycan-containing molecules (e.g., proteoglycans, etc.) (Alcan Blue), and elastins (VanGieson) was observed and the intensity of staining for each layer of the tissues is summarized in Table 7.

TABLE 7

| Layer of unseparated amnion/chorion tissue | H & E | Masson Trichrome | Alcan Blue | VanGieson |
| --- | --- | --- | --- | --- |
| Epithelial layer | +++ | + | + | + |
| Amniotic basement membrane | + | +++ | ++ | + |
| Compact layer | + | +++ | +++ | + |
| Fibroblast layer | + | +++ | ++ | ++ |
| Intermediate layer | + | ++ | ++ | ++ |
| Reticular layer | + | + | + | + |
| Chorionic basement membrane* | | | | |
| Trophoblast layer including capsular decidua | +++ | ++ | + | +++ |

Scoring: +, ++, +++ indicates slight, moderate, and heavy staining, respectively.
*indicates not quantified.

Example 21

Chorion Separation from Amnion and Intermediate Layer

Unseparated amnion/chorion having an intermediate layer is dissected away from the placental disc and placed in a tray with the chorion facing up. The edge of the chorion is gently pulled up using one hand while the other hand secures the amnion with the intermediate layer on the tray. With flattened fingers of one hand on the amnion/intermediate layer securing it to the base of the tray, the other hand holds the chorion close to the line of separation and pulls upwards slowly such that the chorion pulls away from the amnion/intermediate layer over a short distance. This process of peeling away of the chorion is slowly continued by repeating the same securing and pulling actions along the line of separation between the intermediate layer and the chorion until the chorion is separated away leaving the intermediate layer substantially intact on the separated amnion.

The separated amnion with intermediate layer or the separated chorion may be processed using any one of Processes A-K. In addition, the chorion may be separated from the amnion and intermediate layer before, during, or after dissecting, cutting, perforating, or washing.

Example 22

Amnion Separation from Chorion and Intermediate Layer

Unseparated amnion/chorion having an intermediate layer is dissected away from the placental disc and placed in a tray with water to swell the intermediate layer. The excess water is drained away and the unseparated amnion/chorion is oriented with the amnion facing up on the tray. Using forceps, the edge of the amnion is pulled up slightly to visualize the line of separation between the intermediate layer and the amnion. The flat end of a scalpel is then used to gently scrape from the forceps to the line of separation while gently and slowly pulling up with the forceps. This process of scraping and pulling is slowly repeated along the line of separation between the intermediate layer and the amnion until the amnion is separated away leaving the intermediate layer substantially intact on the separated chorion.

The separated chorion with intermediate layer or the separated amnion may be processed using any one of Processes A-K. In addition, the amnion may be separated from the chorion and intermediate layer before, during, or after dissecting, cutting, perforating, or washing.

What is claimed is:

1. An unseparated amnion/chorion sheet having a hemoglobin content of less than about 5 ng per mg of dry mass of the sheet, wherein the unseparated amnion/chorion sheet is dehydrated, and wherein the unseparated amnion/chorion sheet is detached from the placental disc and umbilical cord.

2. The sheet of claim 1, wherein the unseparated amnion/chorion sheet comprises an intermediate layer.

3. The sheet of claim 1, wherein the unseparated amnion/chorion sheet is from a human placenta.

4. The sheet of claim 1, wherein the unseparated amnion/chorion sheet is dehydrated by lyophilization, dehydrated by heat-drying, dehydrated by oven-drying, dehydrated by air-drying, or dehydrated by chemical dehydration.

5. The sheet of claim 1, wherein the unseparated amnion/chorion sheet comprises a marking selected from an embossment, a cut, a stain, a tint, and a stamp.

6. The sheet of claim 1, wherein the unseparated amnion/chorion sheet has a mean thickness ranging from about 70 µm to about 700 µm.

7. The sheet of claim 1, wherein the unseparated amnion/chorion sheet is dehydrated by lyophilization.

8. The sheet of claim 1, wherein the unseparated amnion/chorion sheet has a hemoglobin content of less than about 1 ng/mg of dry mass of the sheet.

9. The sheet of claim 1, wherein the unseparated amnion/chorion sheet has a hemoglobin content of less than about 0.5 ng/mg of dry mass of the sheet.

10. A composition comprising at least one unseparated amnion/chorion sheet, wherein the at least one unseparated amnion/chorion sheet comprises an intermediate layer having a mean thickness of greater than about 5 µm, and wherein the composition has a hemoglobin content of less than about 5 ng per mg of dry mass of the composition, wherein the composition is dehydrated, and wherein the unseparated amnion/chorion is detached from the placental disc and umbilical cord.

11. The composition of claim 10, wherein the composition comprises one or more additional sheets, wherein the one or more additional sheets is selected from a perforated, unseparated amnion/chorion sheet; an unperforated, unseparated amnion/chorion sheet; a perforated, separated amnion sheet; an unperforated, separated amnion sheet; a perforated, separated chorion sheet; and an unperforated, separated chorion sheet.

12. The composition of claim 10, wherein the composition is dehydrated by lyophilization.

13. The composition of claim 10, wherein the composition has a hemoglobin content of less than about 1 ng/mg of dry mass of the composition.

14. The composition of claim 10, wherein the composition has a hemoglobin content of less than about 0.5 ng/mg of dry mass of the composition.

15. A method of treating a wound of a subject comprising applying the sheet of claim 1 to the wound of the subject.

16. The method of claim 15, wherein the wound is a wound of an eye, a wound of the skin, a wound of a nerve, a wound of a tendon, or a wound of the dura.

17. The method of claim 15, wherein the wound is a burn, a laceration, a corneal ulceration, a conjunctival lesion, a diabetic ulcer, a venous ulcer, an arterial ulcer, a decubitus ulcer, or a surgical wound.

18. A method of treating a wound of a subject comprising applying the composition of claim 10 to the wound of the subject.

19. The method of claim 18, wherein the wound is a burn, a laceration, a corneal ulceration, a conjunctival lesion, a diabetic ulcer, a venous ulcer, an arterial ulcer, a decubitus ulcer, or a surgical wound.

* * * * *

UNITED STATES PATENT AND TRADEMARK OFFICE
CERTIFICATE OF CORRECTION

| | |
|---|---|
| PATENT NO. | : 11,413,372 B2 |
| APPLICATION NO. | : 15/760757 |
| DATED | : August 16, 2022 |
| INVENTOR(S) | : John Daniel, Sarah Griffiths and Richard Berg |

It is certified that error appears in the above-identified patent and that said Letters Patent is hereby corrected as shown below:

In the Specification

In Column 26, Line 57, "0.01 nanogram per" should read --0.01 nanograms per--.

In Column 36, Line 6, Table 4, "µg/mg" should read --ng/mg--.

Signed and Sealed this
Eleventh Day of October, 2022

Katherine Kelly Vidal
*Director of the United States Patent and Trademark Office*